(12) United States Patent  
Wang et al.

(10) Patent No.: US 10,342,608 B2  
(45) Date of Patent: Jul. 9, 2019

(54) ABLATION CATHETER SYSTEM AND METHOD FOR DEPLOYING SAME

(71) Applicant: The Board Of Trustees Of The Leland Stanford Junior University, Palo Alto, CA (US)

(72) Inventors: Paul Wang, Saratoga, CA (US); Bryant Lin, Menlo Park, CA (US); Matthew Siljander, Evanston, IL (US)

(73) Assignee: The Board Of Trustees Of The Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/054,755

(22) Filed: Oct. 15, 2013

(65) Prior Publication Data

US 2014/0114304 A1 Apr. 24, 2014

Related U.S. Application Data

(60) Provisional application No. 61/715,784, filed on Oct. 18, 2012.

(51) Int. Cl.
*A61B 18/14* (2006.01)
*A61B 18/00* (2006.01)
*A61B 90/00* (2016.01)

(52) U.S. Cl.
CPC ............ *A61B 18/1492* (2013.01); *A61B 2018/00005* (2013.01); *A61B 2018/0022* (2013.01);

(Continued)

(58) Field of Classification Search
CPC .......... A61B 2018/00267; A61B 2018/00202; A61B 2018/00279; A61B 2018/00982; A61B 2018/00184
See application file for complete search history.

(56) References Cited

U.S. PATENT DOCUMENTS 5,324,284 A * 6/1994 Imran ............................ 606/15
5,571,115 A * 11/1996 Nicholas ................ A61B 17/02
600/204

(Continued)

FOREIGN PATENT DOCUMENTS

| JP | 2010233810 | 10/2010 |
|---|---|---|
| WO | 2010078875 | 7/2010 |
| WO | 2010070766 | 5/2012 |

OTHER PUBLICATIONS

"The CardioFocus Endoscopic Ablation System", CardioFocus. com. http://www.cardiofocus.com/technology_us.html, Copyright 2011 (2 pages).

*Primary Examiner* — Eun Hwa Kim
(74) *Attorney, Agent, or Firm* — Neal Marcus

(57) ABSTRACT

An ablation therapy system is disclosed comprising an ablation catheter system for treating atrial fibrillation (AF). The ablation catheter system comprises a catheter body including a lumen for receiving a visualization catheter, an ablation element for ablating tissue in a patient's heart having abnormal electrical activity, a support assembly for supporting the ablation element, the support assembly being supported by the catheter assembly. The support assembly includes a lumen to receive the visualization catheter, wherein the support assembly is configured to rotate and/or pivot with respect to the catheter body.

21 Claims, 12 Drawing Sheets

(52) U.S. Cl.
CPC ............... *A61B 2018/00029* (2013.01); *A61B 2018/00184* (2013.01); *A61B 2018/00202* (2013.01); *A61B 2018/00267* (2013.01); *A61B 2018/00279* (2013.01); *A61B 2018/00285* (2013.01); *A61B 2018/00351* (2013.01); *A61B 2018/00357* (2013.01); *A61B 2018/00577* (2013.01); *A61B 2018/00791* (2013.01); *A61B 2018/00821* (2013.01); *A61B 2018/00839* (2013.01); *A61B 2018/00982* (2013.01); *A61B 2090/065* (2016.02); *A61B 2218/002* (2013.01)

(56) References Cited

U.S. PATENT DOCUMENTS

| | | | |
|---|---|---|---|
| 5,740,808 A | | 4/1998 | Panescu et al. |
| 5,885,278 A * | | 3/1999 | Fleischman ........ A61B 18/1492 600/374 |
| 6,165,169 A * | | 12/2000 | Panescu et al. ............... 606/1 |
| 6,233,491 B1 * | | 5/2001 | Kordis et al. ................. 607/122 |
| 6,572,612 B2 | | 6/2003 | Stewart et al. |
| 6,605,055 B1 | | 8/2003 | Sinofsky et al. |
| 6,626,900 B1 | | 9/2003 | Sinofsky et al. |
| 6,652,515 B1 | | 11/2003 | Maguire et al. |
| 6,658,279 B2 * | | 12/2003 | Swanson et al. ............. 600/407 |
| 6,780,183 B2 | | 8/2004 | Jimenez et al. |
| 7,410,486 B2 | | 8/2008 | Fuimaono et al. |
| 7,591,832 B2 | | 9/2009 | Eversull et al. |
| 7,727,228 B2 | | 6/2010 | Abboud et al. |
| 7,727,229 B2 | | 6/2010 | He et al. |
| 7,736,362 B2 | | 6/2010 | Eberl et al. |
| 7,740,627 B2 | | 6/2010 | Gammie et al. |
| 7,765,014 B2 | | 7/2010 | Eversull et al. |
| 7,850,685 B2 | | 12/2010 | Kunis et al. |
| 7,993,350 B2 | | 8/2011 | Ventura et al. |
| 8,016,748 B2 | | 9/2011 | Mourlas et al. |
| 8,050,746 B2 | | 11/2011 | Saadat et al. |
| 2001/0020126 A1 | | 9/2001 | Swanson et al. |
| 2002/0087208 A1 | | 7/2002 | Koblish et al. |
| 2003/0065371 A1 * | | 4/2003 | Satake .......................... 607/102 |
| 2003/0208195 A1 | | 11/2003 | Thompson et al. |
| 2004/0006333 A1 | | 1/2004 | Arnold et al. |
| 2004/0243124 A1 | | 12/2004 | Im et al. |
| 2004/0260277 A1 | | 12/2004 | Maguire |
| 2005/0085841 A1 | | 4/2005 | Eversull et al. |
| 2005/0228452 A1 | | 10/2005 | Mourlas et al. |
| 2006/0241366 A1 * | | 10/2006 | Falwell et al. ................. 600/374 |
| 2006/0271032 A1 | | 11/2006 | Chin et al. |
| 2007/0015964 A1 | | 1/2007 | Eversull et al. |
| 2007/0083194 A1 * | | 4/2007 | Kunis et al. ..................... 606/41 |
| 2007/0106292 A1 * | | 5/2007 | Kaplan et al. ................... 606/41 |
| 2008/0183036 A1 | | 7/2008 | Saadat et al. |
| 2008/0281312 A1 | | 11/2008 | Werneth et al. |
| 2009/0112199 A1 | | 4/2009 | Zhang et al. |
| 2009/0143640 A1 | | 6/2009 | Saadat et al. |
| 2009/0227999 A1 | | 9/2009 | Willis et al. |
| 2009/0299354 A1 | | 12/2009 | Melsky et al. |
| 2010/0130836 A1 | | 5/2010 | Malchano et al. |
| 2010/0204561 A1 | | 8/2010 | Saadat et al. |
| 2010/0256629 A1 | | 10/2010 | Wylie et al. |
| 2010/0261990 A1 | | 10/2010 | Gillis et al. |
| 2010/0292558 A1 | | 11/2010 | Saadat et al. |
| 2011/0034790 A1 | | 2/2011 | Mourlas et al. |
| 2011/0054548 A1 | | 3/2011 | Hestad et al. |
| 2011/0082451 A1 | | 4/2011 | Melsky |
| 2011/0106074 A1 | | 5/2011 | Kunis et al. |
| 2011/0152855 A1 * | | 6/2011 | Mayse et al. ..................... 606/33 |
| 2011/0184400 A1 | | 7/2011 | Pageard |

* cited by examiner

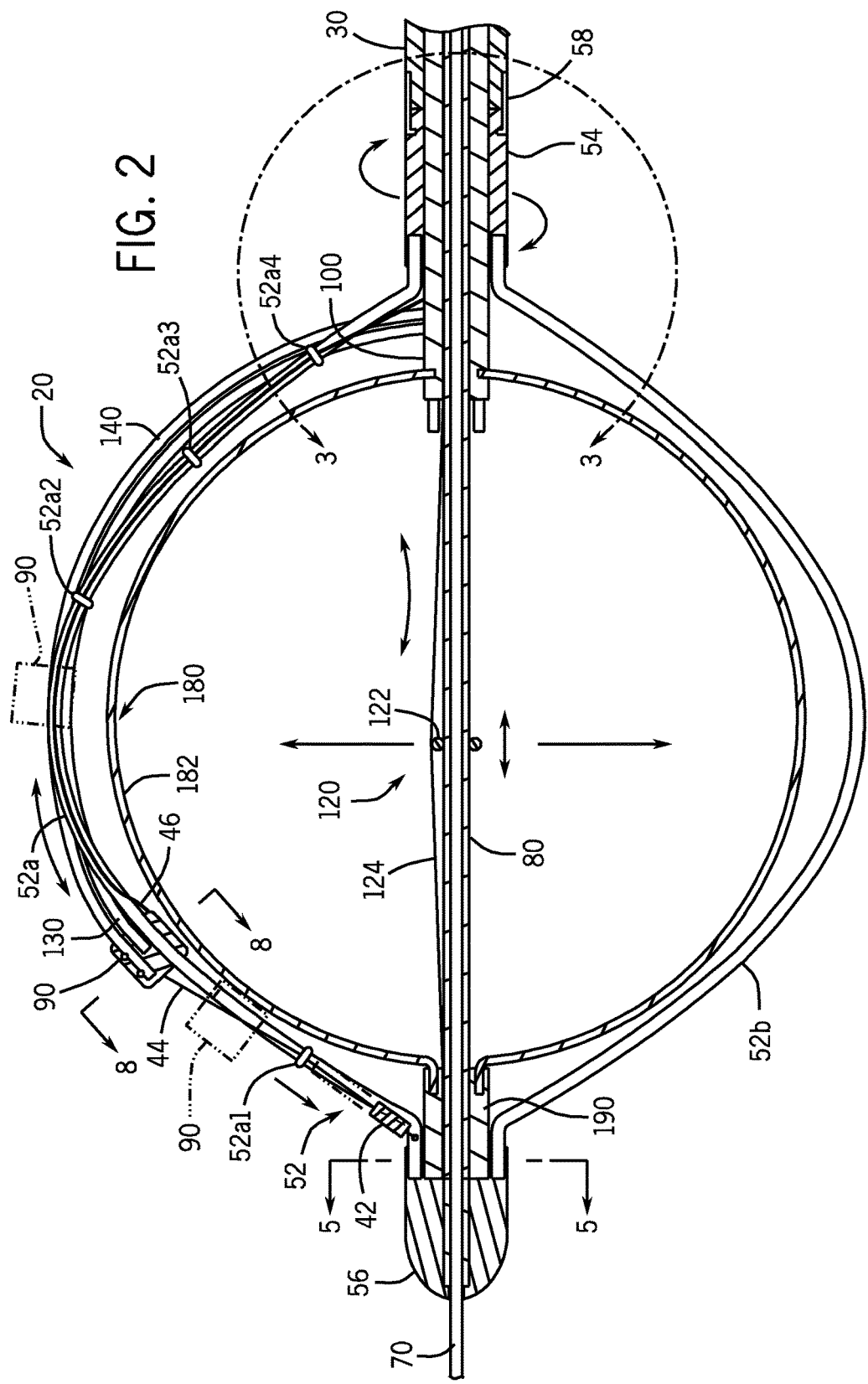

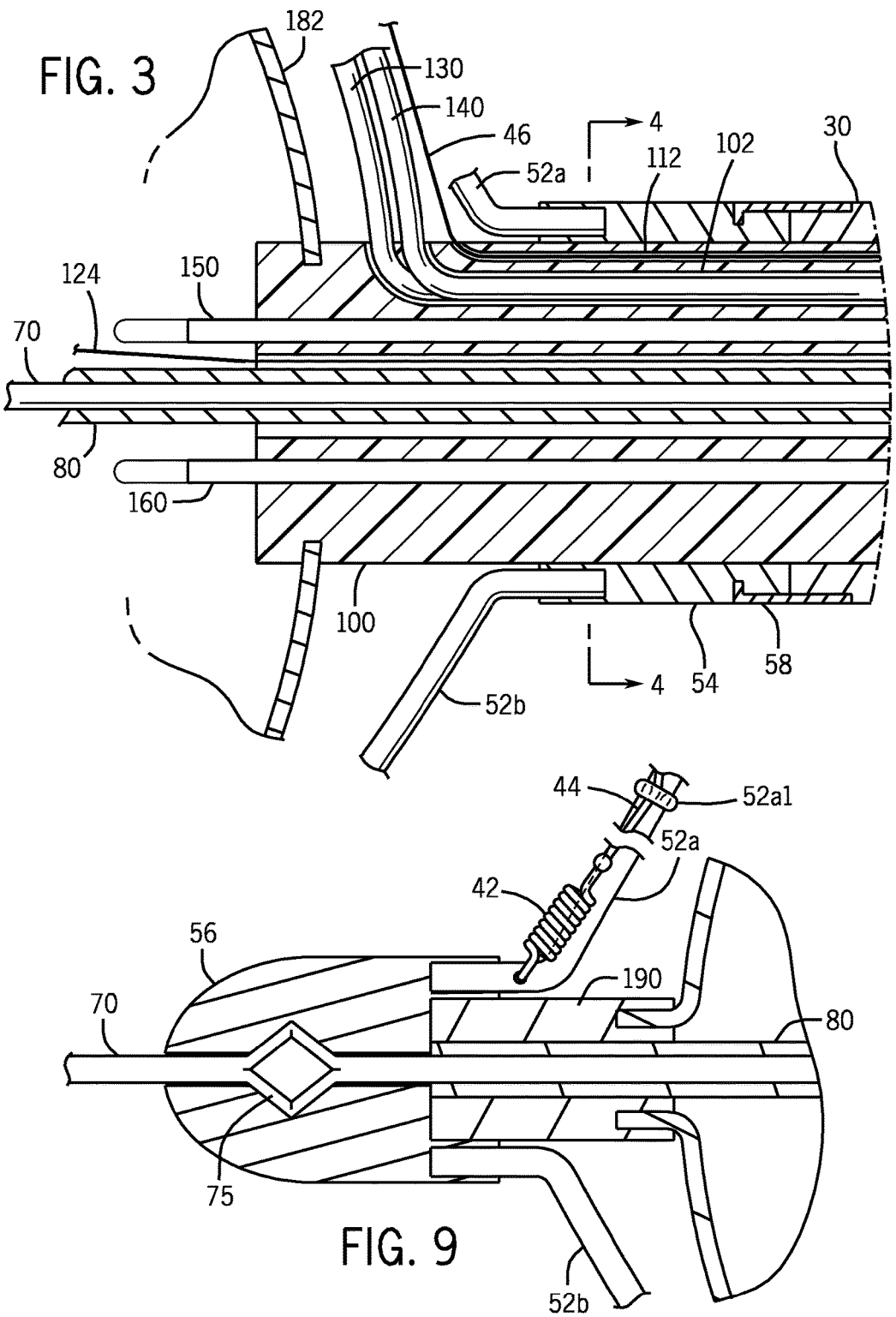

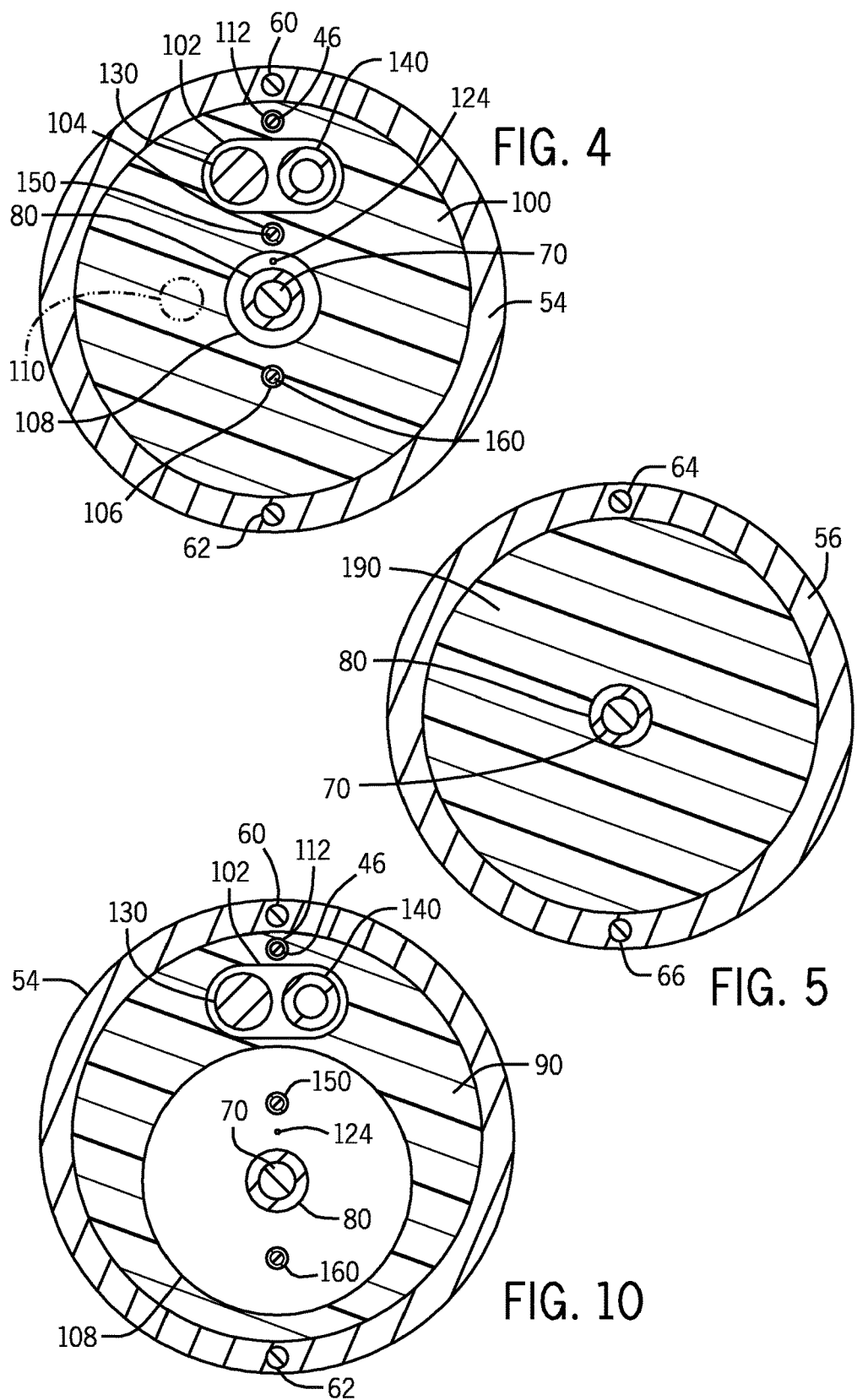

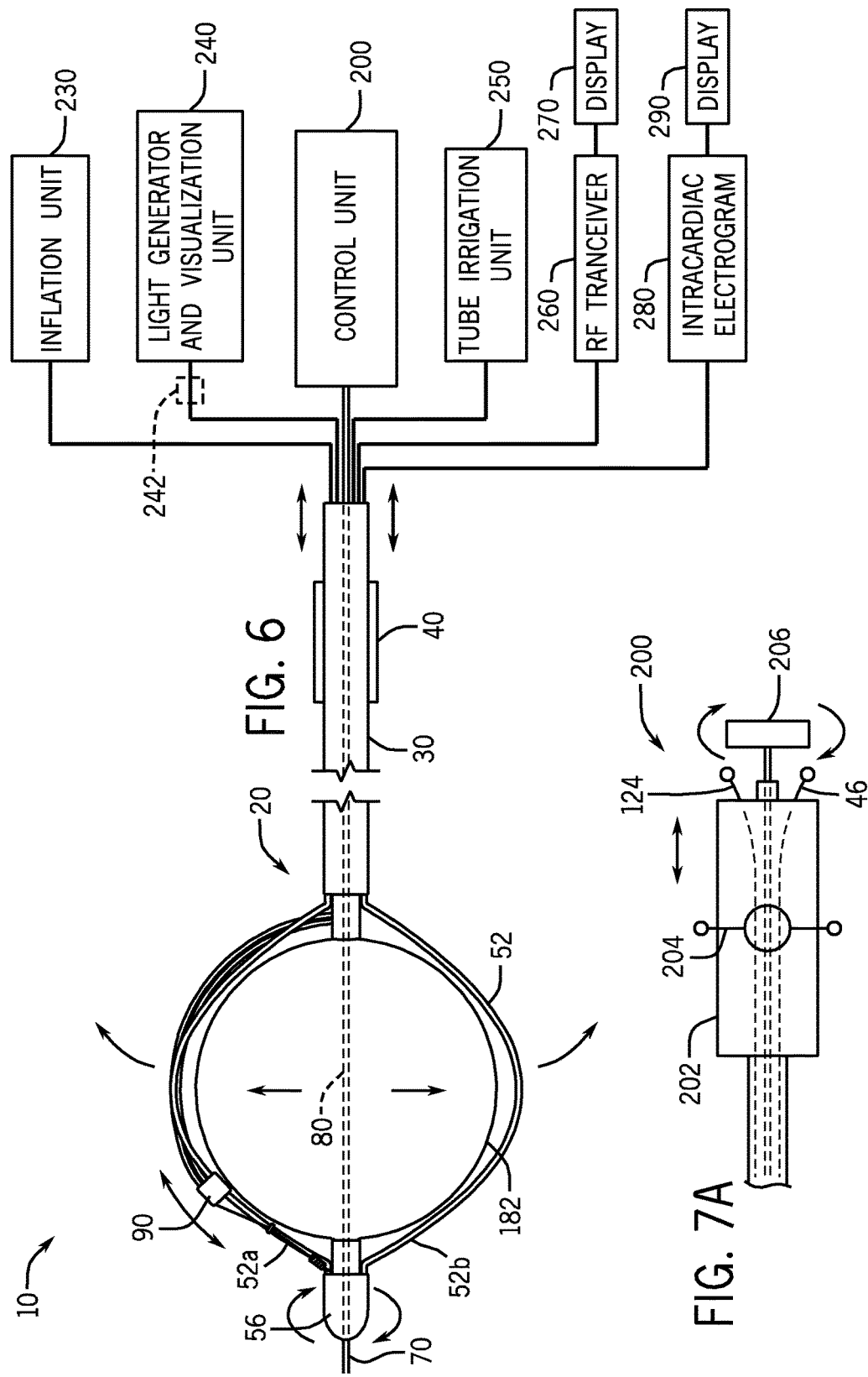

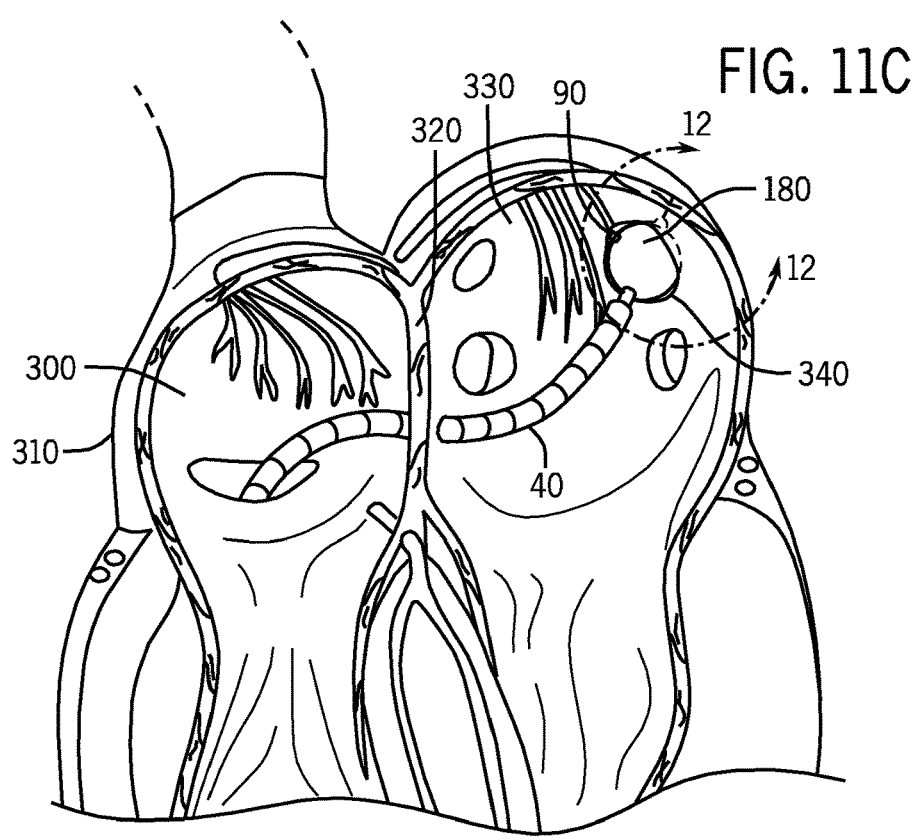
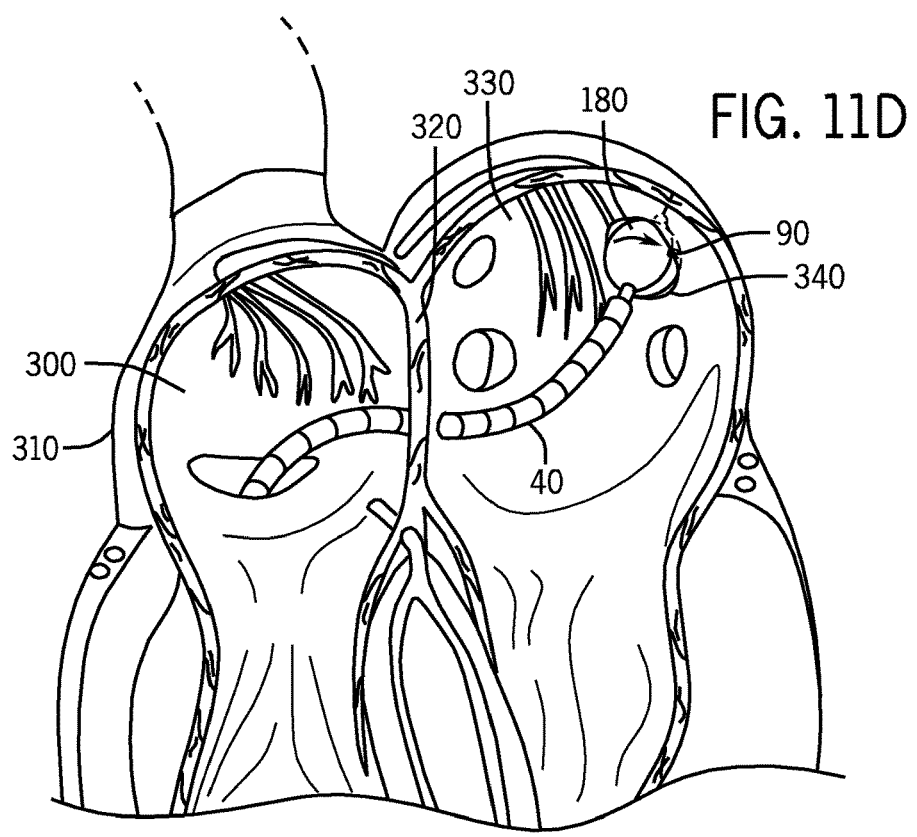

ABLATION CATHETER SYSTEM AND METHOD FOR DEPLOYING SAME

CROSS-REFERENCE TO RELATED APPLICATIONS

This application claims priority to U.S. provisional application Ser. No. 61/715,784, filed Oct. 18, 2012, which is incorporated by reference herein.

FIELD OF THE INVENTION

The present invention relates to an ablation catheter system and method for deploying the same.

BACKGROUND OF THE INVENTION

Atrial fibrillation ("AF") is a form of cardiac arrhythmia. "Atrial" refers to the top two chambers of the heart known as the atria, where irregularity in AF occurs. The atria are designed to send blood efficiently and rhythmically into the ventricles by way of regular electrical signals. From there, blood is pumped to the rest of the body. In AF, the electrical signals are rapid, irregular and disorganized, and the heart may not pump as efficiently. Individuals with AF have an increased risk of stroke. Stroke occurs if a piece of a blood clot in the atria leaves the heart and becomes lodged in an artery in the brain.

Current AF treatment options are not perfect. A medical practitioner may use medication as a treatment option. Medication, however, only assists in the management of the symptoms. It is not a cure for AF. Medication can also present side effects that may be more dangerous than AF itself. Another treatment option is electrical cardioversion. In certain circumstances, electrical cardioversion may be used to restore normal heart rhythm with an electric shock, but this option often results in AF reoccurrence.

When medication is not successful, the medical practitioner may treat AF with ablation catheter therapy. In this procedure, a catheter with an ablation element is introduced through a blood vessel and directed to the atria in the heart muscle. The medical practitioner will localize a specific area of cardiac tissue having aberrant electrically conductive pathways and emitting or conducting erratic electrical impulses. The medical practitioner will then deliver a burst of radio frequency (RF) energy to destroy the tissue that triggers abnormal electrical signals or to block abnormal electrical pathways. In AF, it has been shown that the source of the electrical abnormality is at the opening of each of the four pulmonary veins that come off the left atrium. The medical practitioner therefore targets these openings for ablation catheter therapy.

While the ablation catheter therapy has become more widely adopted, it is not without its difficulties. In order to effectively treat AF with this procedure, accurate placement and line formation of the lesions (i.e., adjacent lesions without gaps) are critical. Specifically, the success of atrial fibrillation ablation is dependent upon the creation of lesions that adequately disrupt the tissue's electrical properties. Current techniques do not permit the medical practitioner (operator) to determine exactly where the lesions have been made and whether energy has been efficiently delivered. The medical practitioner relies primarily on changes in electrical signals, which are interpreted as signs of adequate ablation but frequently result in restoration of electrical function after the ablation, and induced edema thus restores. In sum, accurate placement and line formation of ablation lesions are tough to achieve because visualization is inadequate. Consequently, it is thus difficult to effectively treat cardiac arrhythmias such as AF with current ablation technologies and methods. Improved methods and systems are thus needed to determine where ablation lesions have been made and whether the lesions are likely to be long-standing.

SUMMARY OF THE INVENTION

An ablation catheter system and method for deploying the same is disclosed.

In accordance with an embodiment of the present invention, an ablation therapy system is disclosed including an ablation catheter system for treating atrial fibrillation (AF), the ablation catheter system comprising: a catheter body including a lumen for receiving a visualization catheter; an ablation element for ablating tissue in a patient's heart having abnormal electrical activity; a support assembly for supporting the ablation element, the support assembly being supported by the catheter body, the support assembly including a lumen to receive the visualization catheter, wherein the support assembly is configured to rotate and/or pivot with respect to the catheter body.

In accordance with yet another embodiment of the present invention, an ablation therapy system is disclosed comprising: (a) an ablation catheter system for treating atrial fibrillation (AF), the ablation catheter system comprising: a catheter body having a lumen for receiving a visualization catheter; an ablation element for ablating tissue in a patient's heart having abnormal electrical activity; and a support assembly for supporting the ablation element, the support assembly being supported by the catheter body, the support assembly including a lumen to receive the visualization catheter, wherein the support assembly is configured to rotate and/or pivot with respect to the catheter body; and (b) a control unit for controlling the support assembly, thereby enabling a user to coordinate rotation and/or pivoting of the support assembly with respect to the catheter body.

In accordance with yet another embodiment of the present invention, an ablation catheter system is disclosed for treating atrial fibrillation (AF), the ablation catheter system comprising: a catheter body including a lumen for receiving a visualization catheter; an ablation element for ablating tissue in a patient's heart having an abnormal electrical activity; and a support assembly for supporting the ablation element, the support assembly being supported by the catheter body, the support assembly including a lumen to receive the visualization catheter, wherein the ablation element is configured to move along the support assembly.

In accordance with yet another embodiment of the present invention, a method is disclosed of treating atrial fibrillation, the method comprising: providing an ablation therapy system including an ablation catheter system, the catheter system comprising a catheter body having a lumen for receiving a visualization catheter, an ablation element, a support assembly for supporting the ablation element, the support assembly supported by the catheter body for receiving the visualization catheter, the support assembly including a support arm; advancing the ablation catheter system into a heart of a patient; and maneuvering the ablation element to contact tissue of the heart by controlling the support assembly to cause it to pivot and/or rotate with respect to the catheter body.

BRIEF DESCRIPTION OF THE DRAWINGS

FIG. 2 depicts a cross-sectional view of the ablation catheter system in FIG. 1.

FIG. 3 depicts an enlarged cross-section view of the ablation catheter system within circle line 3-3 in FIG. 2.

FIG. 4 depicts a cross-sectional view of an ablation catheter system along line 4-4 in FIG. 3.

FIG. 5 depicts a cross-sectional view of an ablation catheter system along line 5-5 in FIG. 2.

FIG. 6 depicts a side view of the ablation therapy system including the ablation catheter system of FIG. 1 and the external operational components for operating the ablation catheter system.

FIG. 7A depicts the control unit in FIG. 6 in accordance with an embodiment of the present invention.

FIG. 9 depicts an enlarged side view of the distal section of the ablation catheter system of FIG. 1 in accordance with an alternative embodiment of the present invention.

FIG. 10 depicts a cross-sectional view of an ablation catheter system along line 5-5 in FIG. 2 in accordance with another embodiment of the present invention.

FIGS. 11A-11E depict selected application steps of a method of using the ablation therapy system in FIG. 6.

DETAILED DESCRIPTION OF THE INVENTION

Figure 1:
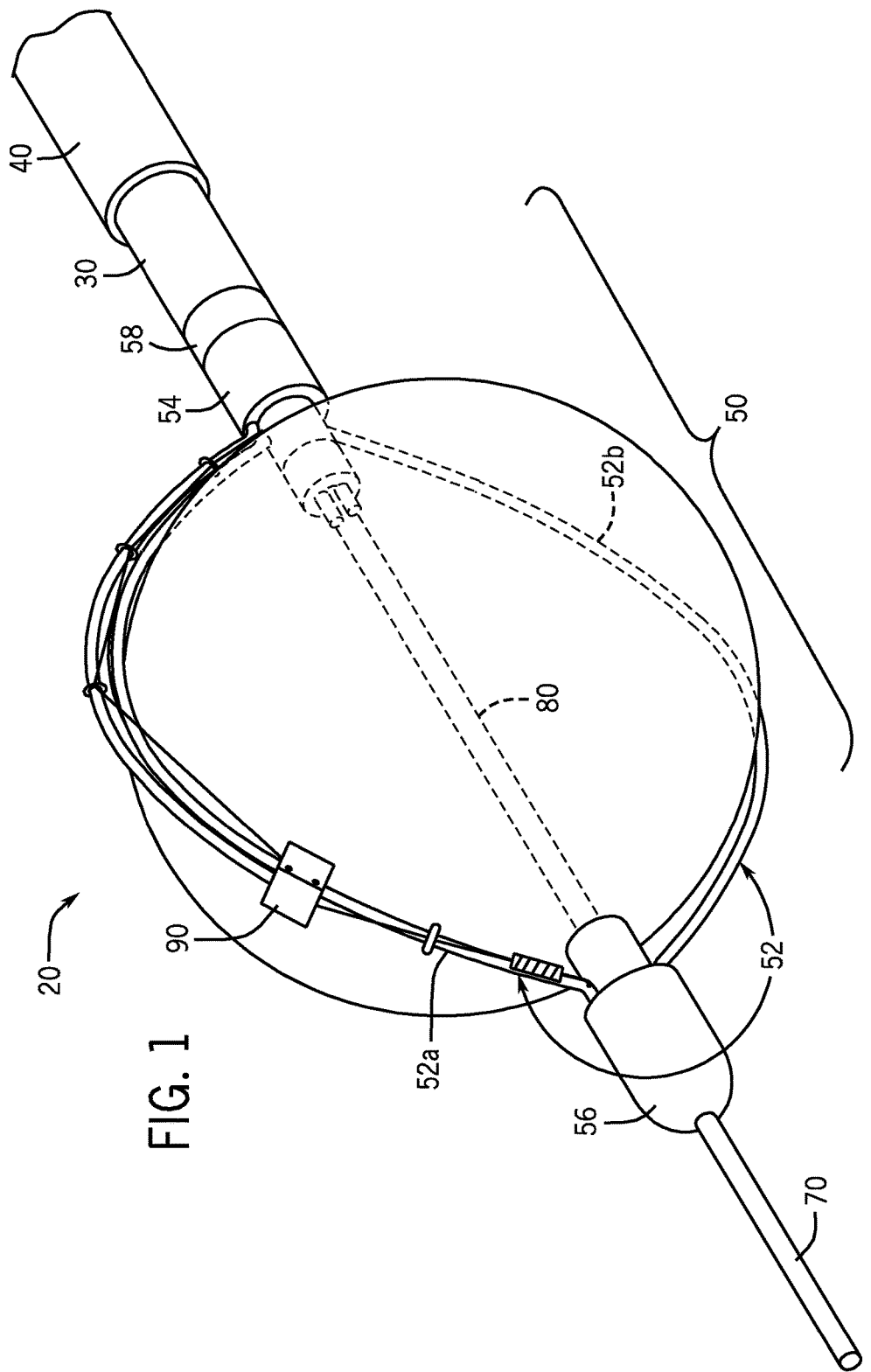
FIG. 1 depicts a perspective view of the ablation catheter system for treating AF in accordance with an embodiment of the present invention.

Ablation therapy system 10 includes ablation catheter system 20. FIG. 1 depicts a perspective view of ablation catheter system 20 for treating AF in accordance with an embodiment of the present invention. FIG. 2 depicts a cross-sectional view of ablation catheter system 20 in FIG. 1. FIG. 3 depicts an enlarged cross-section view of ablation catheter system 20 within circle line 3-3 in FIG. 2.

Ablation catheter system 20 includes catheter body 30, catheter sheath 40, support assembly 50, central guidewire 70, central guidewire sheath 80 and RF ablation element 90 and visualization catheter 100. Support assembly 50 actually supports ablation element 90 as discussed in more detail below.

Catheter body 30 has a central inner lumen 31 for receiving visualization catheter 100. Catheter body 30 is preferably constructed of plastic with an inner lumen 31 diameter that is just slightly larger than the diameter of visualization catheter 100 to enable it to pass through. In one embodiment, catheter body 30 has an outer diameter of 4 mm and visualization catheter 100 has an outer diameter of 2.6 mm while the central lumen of the catheter body 30 has a diameter of just slightly larger than 2.6 mm. However, those skilled in the art know than various dimensions of the catheter body 30 and visualization catheter 100 may be designed to achieve desired results.

Support assembly 50 includes support arms 52, rear ring 54 and front ring 56. Rear ring 54 mates with (and supported by) catheter body 30 by way of mating ring 58. Specifically, rear ring 54 has an annular recess to receive an annular projection of mating ring 58. Rear ring 54 engages with mating ring 58 in a key configuration as clearly shown in FIGS. 2 and 3 to enable rear ring 54 to rotate with respect to catheter body 30. Rear and front rings 54 and 56 each have two opposing blind holes 60, 62 and 64, 66 respectfully, for receiving support arms 52. Rear ring 54 includes a lumen 55 that extends through the entire length of ring 54 for receiving visualization catheter 100.

Front ring 56 includes a recessed portion with a corresponding diameter as catheter end 190 discussed below of visualization catheter 100 for receiving the front end of visualization catheter 100. As seen in FIG. 2, this recessed portion only extends through a portion of front ring 56. Front ring 56 includes a lumen of smaller diameter that extends through the entire length of the front ring 56. This lumen diameter is sized for receiving central guidewire 70. Rear and front rings 54, 56 are preferably each about 5-6 mm in length with an outer diameter of approximately 4 mm. Rear ring 54 has an inner lumen diameter of approximately 2.6 mm for receiving visualization catheter 100. Front ring 56 has a recess diameter of 2.6 mm. However, those skilled in the art know that various dimensions may be used to achieve desired results.

In the embodiment shown, support arms 52 comprise two wires 52a, 52b (also referred to as framework wires 52a, 52b) as shown in FIGS. 1-3 (for example). However, those skilled in the art know that support arms 52 may consist of any number of wires or any other structure to support ablation element 90 as described herein. Wires 52a, 52b each have opposing ends that are press fit (proximally) within blind holes 60, 62 and (distally) within blind holes 64,66, respectively for a secure mounting to rear and front rings 54, 56. This is best shown in FIG. 3 as described above, FIG. 4 wherein a cross-sectional view of an ablation catheter system is depicted along line 4-4 in FIG. 3 and FIG. 5 wherein a cross-sectional view of an ablation catheter system depicted along line 5-5 in FIG. 2. Wires 52a, 52b (of support arms 52) are resiliently biased and selectively moveable from a generally linear transport configuration (i.e., internally constrained by the interior walls of sheath 40) to a deployed configuration (i.e., unconstrained when sheath 40 is retracted). This is described in more detail below.

Ablation catheter system 20 further includes a plurality of constraining rings 52a1-52a4 spaced along wire 52a for receiving different control lines as described in detail below. Rings 52a1-54a1 are preferably configured around wire 52a (concentrically or non-concentrically), but may also be connected to a side of wire 52a as known to those skilled in the art. In the embodiment shown, four rings are incorporated. Ring 52a1 is spaced along wire 52a in the left quadrant of wire 52a when it is in expanded form (near front ring 56). Rings 52a2-52a4 are spaced along wire 52a in the right quadrant of wire 52a when it is in its expanded form. In the embodiment shown, rings 52a1-52a4 are positioned to enable ablation element 90 to travel between ring 52a1 and ring 52a2. This distance represents approximately 50% of the length of exposed wire 52a (majority of movement in the left 90 degree quadrant when wire 52a is expanded). However, those skilled in the art know that the number, size and position of the rings are chosen to ensure that (1) the control lines do not interfere with the balloon (described below), (2) the rings do not interfere with ablation element 90 when it travels along a portion of wire 52a to achieve proper ablation and (3) the rings do not interfere with ablation catheter system 20 when it is deployed from sheath

40. Rings 52a1-52a4 are preferably formed as part of wire 52a or may be subsequently attached to it.

Figure 8:
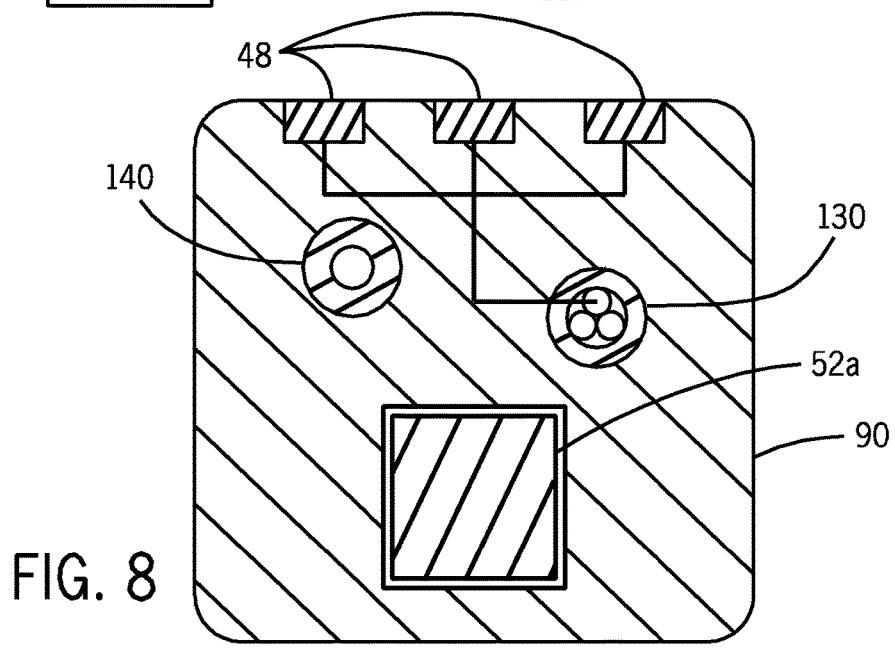
FIG. 8 depicts an enlarged cross-sectional view of the ablation element along line 8-8 in FIG. 2.

Ablation element 90 comprises an electrode as known to those skilled in the art. Ablation element 90 has a design that allows delivery of energy to the tissue through its top surface. Ablation element 90 is also used to measure temperature, optionally measure electrical activity of the tissue location and measure pressure against the tissue as described below. As indicated above, support assembly 50 actually supports ablation element 90. In this embodiment, ablation element 90 is mounted in a position to slide along wire 52a as shown. In detail, ablation element 90 includes a lumen located near the bottom thereof that extends through element 90 for receiving one of wires 52a, 52b (support assembly 50) as shown. The lumen shape corresponds in shape to wire 52a as best shown in FIG. 8. Wires 52a, 52b are preferably square in shape, but they may be any shape so long as they prevent ablation element 90 from rotating around or sliding off wire 52a when ablation element 90 is translated. That is, ablation element 90 is adapted to slide or travel along wire 52a (of support arms 52). When the wire is rotated, however, ablation element 90 also simultaneously moves with wire 52a but without rotating. This will ensure that the top face of ablation element 90 is always facing outwardly towards the tissue to be ablated. Ablation element 90 is thus capable of moving with wire 52a as well as slide along wire 52a as described in more detail below.

Ablation catheter system 20 further includes spring 42, tension line 44 and pull line 46. Tension line 44 and pull line 46 are connected to opposing sides of ablation element 90. Tension line 44 and pull line 46 each have an end that is secured or tied to ablation element 90 by way of link, hook, ring or other mechanism as known to those skilled in the art, on opposing sides of ablation element 90. Alternatively, epoxy suitable for surgery may be used to secure tension line 44 and pull line 46 to ablation element 90 as known to those skilled in the art. Spring 42 has two ends, one of which is linked through a hole in wire 52a adjacent front ring 56 while the other end is attached to the end of tension line 44. While tension line 44 is employed, the end of spring 42 may extend a sufficient length and material to act as the tension line itself, which is attached directly to ablation element 90. Tension line 44 is threaded through constraining ring 52a1 along wire 52a to constrain or maintain the line position along wire 52a. Pull line 46 is threaded through constraining rings 52a2-52a4 so that pull line 46 substantially follows the shape of wire 52a. Pull line 46 leaves constraining ring 52a4 and extends through a lumen within visualization catheter 100 described below. In short, pull wire 46 is pulled to slide ablation element 90 along wire 52a while spring 42 maintains tension on tension line 44 (and hence ablation element 90) to enable accurate control of ablation element 90. When wires 52a, 52b are rotated, pull line 46 is adjusted to permit adequate movement of such wires.

It is important that the lumen for receiving wire 52a is designed to be located near the bottom of ablation element 90 to allow maximum contact between a balloon (or other expandable structure as described below) and wire 52a (of support arms 52). Such a construction will provide for a better imaging from visualization equipment located within the balloon (as described in detail below). Ablation element 90 also includes a bore to allow the entry of RF irrigation tubing (as also discussed in detail below). Tiny holes are drilled into the sides of this ablation element 90 near the top surface to release cooling saline when energy is being delivered. Ablation element 90 is depicted as showing two exit ports per side, but those skilled in the art know that any number of ports may be used. Once saline enters ablation element 90, saline exits the tiny exit ports by a channel that has been bored through the middle thereof that connects the exits ports with the saline entry lumen. Ablation element 90 further includes one or more pressure sensors 48 preferably located along the top surface of ablation element 90 as shown in FIG. 8 for sensing the pressure of ablation element 90 against heart tissue. Sensors 48 are coupled to RF and thermocouple wires as discussed below.

In the embodiment shown, wires 52a, 52b are preferably made of Nitinol for their deformable but yet memory-retaining properties, but those skilled in the art know that other alloys (or other materials) are possible to achieve the same effect. Wires 52a, 52b are heat treated to a curved height to match the standard size of a pulmonary vein ostium. The lengths of wires 52a, 52b are designed to be slightly longer than the blind holes of rings 54,56 when the wires (or other type of support arms 52) are under minimal stress (when sheath 40 is retracted). The standard curve size is approximately 27 mm or less and the wire length is approximately 32 mm. However, those skilled in the art know that the length and curve size of wires 52a, 52b may be varied to achieve desired results. While two wires (52a, 52b) and one RF ablation element are shown and described herein, those skilled in the art know that any number of wires (or other support arms 52) and any number of ablation elements may be used to achieve desired results. These RF ablation elements may be configured as an array or other configuration. As indicated above, ablation element 90 is adapted to slide along arm 52a in the embodiment shown in the figures. However, those skilled in the art know that ablation element 90 may be designed to be fixed to wire 52a to achieve desired results (in an alternative embodiment).

Central guidewire 70 extends completely through the ablation catheter system 20. In the embodiment shown in FIGS. 1-5, central guidewire 70 is fixed to front ring 56 within a lumen 68. Guidewire 70 also extends outside of front ring 56 to assist in the guidance of ablation catheter system 20. By retracting guidewire 70 (pulling it more proximally) while holding catheter body 30), the radius of curvature of wires 52a, 52b (support arms 52) increases. This causes such wires to further expand to reach a wall of the pulmonary vein, if necessary. Rotating guidewire 70 rotates front ring 56, thereby simultaneously rotating wires 52a, 52b (support arms 52), ablation element 90 and rear ring 54 to enable the medical practitioner to ablate tissue around the ostium of a pulmonary vein.

In order to ablate a lesion line around the ostium, ablation catheter system 20 must operate over 360 degrees (in complete rotation or 180 degrees in opposite directions). In the embodiment shown, guidewire 70 may be rotated 180 degrees in both directions to achieve a complete 360 degree ablation line. (Sets of RF and thermocouple wires 130 and irrigation tubing 140 are coupled to ablation element 90 as described below.) In brief, thermocouple wires 130 and irrigation tubing 140 have sufficient slack to enable wires 52a, 52b to move and rotate 180 degrees in either direction. When catheter sheath 40 is retracted back over wires 52a, 52b (support arms 52), guidewire 70 and front ring 56 are in its most forward position with respect to the catheter body 30. Guidewire 70 has a diameter that preferably measures 0.03 inches, but those skilled in the art know that this diameter may be varied to achieve a desired result. Guidewire 70 may be rotated, retracted and fixed in position using a control unit as described in more detail below.

Ablation catheter system 20 further includes pivot mechanism 120. Pivot mechanism 120 is configured to cause wires 52a, 52b to pivot with respect to catheter body 30. Pivot mechanism 120 includes O-ring 122 secured around sheath 80, midway between the rear ring 54 and catheter end 190 and a flexible line. Pivot mechanism 120 offers the medical practitioner greater control over wires 52a, 52b to position ablation element 90 at desired locations. Pivot mechanism 120 may be retracted and fixed in position using a control unit as described in more detail below.

As indicated above, ablation element 90 may slide along wire 52a, expand outwardly, rotate and ultimately pivot. Because of this range of motion, lateral and vertical movement of ablation element 90 may be coordinated to create a more accurate ablation lesion line (including diagonally) in the heart tissue.

Ablation catheter system 20 also includes RF and thermocouple wires 130 for delivering energy, measuring temperature at the RF ablation element 90, measuring the pressure of the ablation element 90 against heart tissue and measuring electrical activity of the localized heart tissue. RF and thermocouple wires 130 are coupled to, i.e., extend within ablation element 90 as shown. RF and thermocouple wires 130 supply RF energy to the ablation element 90 for ablation. A wire line that splits off of wires 130 is coupled directly to pressure sensors 48 to achieve pressure sensing. Another wire line that splits off of wires 130 that is coupled to one or more sensors or other technology (part of RF ablation element 90, but not shown) for sensing electrical activity and/or temperature of the heart tissue as known to those skilled in the art. In other embodiments, those skilled in the art know that additional sensors for sensing tissue conditions may be mounted on support arms 52. Ablation catheter system 20 also includes RF saline irrigation tubing 120 for delivering cooling fluid to ablation element 90 via bores within ablation element 90 as described above.

Ablation catheter system 20 further includes light source 150 and visualization source 160 to provide light and to enable a medical practitioner to visualize the region and target ablation sites. Light source 150 and visualization source 160 run through visualization catheter 100 and extend outwardly from it as described in more detail below. Light source 150 is preferably a fiber optic cable/wires as known by those skilled in the art to transmit light. When wishing to view the tissue wall, light is used to illuminate the distal end of light source 150. Visualization source 160 is also preferably a fiber optic cable/wires, but the cable/wires incorporates a lens located distally at the end thereof. The distal ends of light source 150 and visualization source 160 are located within balloon 182 (expandable structure 180) as described in more detail below. While sources 150 and 160 are described as a fiber optic cable/wires, those skilled in the art know that other materials or mechanisms may be used to transmit light and visualize a target site. For example, visualization source 160 may also be a camera. In addition, in alternative embodiments, more than one light source 150 and/or visualization source 160 may be incorporated with an adequate number of lumens for such sources. For example, a CMOS sensor (complementary metal-oxide semiconductor sensor) that is coupled to a fiber optic cable may be employed as known to those skilled in the art. The CMOS sensor will act as a camera as known to those skilled in the art. In addition, an endoscope may be employed if required. The endoscope will extend through a lumen and sheath within visualization catheter 100 as discussed in more detail below. While visualization source 160 is employed within balloon 182 to visualize a desired region, those skilled in the art know that other visualization components may be used for visualizing a region, and such components may be mounted outside balloon 182 (alternative embodiments). For example, ablation catheter system 20 may include a CMOS sensor mounted to a side of RF ablation element 90 or a support arm 52. The CMOS sensor acts as a camera as described above. Fiber optic cables will be used to couple the CMOS sensor to an external unit with display as known to those skilled in the art.

As discussed briefly above, RF and thermocouple wires 130 are coupled to ablation element 90 and connected to an energy delivery unit that also measures and displays energy delivery, time, temperature, ablation sensor pressure and electrical activity of the heart tissue. RF and thermocouple wires 130 run through a lumen within visualization catheter 100. Wires 130 exit distally out rear ring 54 and run along wire 52a until it reaches ablation element 90. As indicated above, RF and thermocouple wires 130 have sufficient slack between exit point from visualization catheter 100 and ablation element 90, to provide sufficient clearance necessary to enable ablation element 90 to rotate 180 degrees in each direction. Wires 130 are encompassed in a sheath and sized approximately 0.5 mm in diameter. However, those skilled in the art know that the diameter may be varied in size to achieve desired results.

RF irrigation tubing 140 runs next to and in the same lumen as RF and thermocouple wires 130 within visualization catheter 100. It follows the same course, exit and attachment as described for RF and thermocouple wires 130. The purpose is to deliver cooling saline or other fluid to ablation element 90 when it is delivering energy to the tissue. RF irrigation tubing 140 is flexible and it is fluidly coupled to a tub irrigation unit as described in more detail below. In one embodiment, the outer diameter of RF irrigation tubing 140 is approximately 0.5 mm, but those skilled in the art know that other diameter measurements may be used to achieve the desired results.

Visualization catheter 100 includes a plurality of lumens that extend from proximal end (near medical practitioner) to a distal end thereof adjacent rear ring 54. FIG. 4 illustrates these lumens in detail. In particular, visualization catheter 100 includes lumen 102 for receiving RF and thermocouple wires 130 and RF irrigation tubing 140. Visualization 100 further includes lumens 104, 106 for receiving light source 150 and visualization source 160, respectfully. In the embodiment shown in FIGS. 1-4, lumens 104, 106 each include a sheath. These sheaths extend distally from the end of visualization catheter 100 within balloon 182 (discussed below). Light source 150 and visualization source 160 each have a diameter that is appropriately sized to move freely within the sheaths inside lumens 104, 106. The sheaths are employed to prevent fluid from escaping balloon 182 and returning down lumens 104 and 106 (leakage near the medical practitioner). The sheath will be made of an opaque material to enable light to illuminate a region and enable a medical practitioner to visualize a target tissue site using visualization source 160. In an alternative embodiment, light source 150 and visualization source 160 may be fixed within lumens 104, 106 (without a sheath). This also ensures that fluid will not escape and return down lumens 104, 106. In this respect, light source 130 and visualization source 160 extends sufficiently into expandable structure 180 to enable a medical practitioner to visualize virtually all targeted tissue sites.

Visualization catheter 100 further includes lumen 108 that is large enough to receive central guidewire sheath 80 (and guidewire 70) while allowing fluid delivery around central guidewire sheath 80 to inflate an expandable structure 180 such as a balloon as described below. This is clearly shown in FIG. 4. Visualization catheter 100 may optionally include a lumen 110 (dotted lines in FIG. 4) that extends the length of visualization catheter 100 to receive an endoscope (not shown). The endoscope may be employed to provide an additional source for accurate viewing. Lumen 110 may also incorporate an endoscope sheath that extends beyond the end of visualization catheter 100 into expandable structure 180 (described in more detail below). The sheath will also be composed of a material that is opaque (at the distal end thereof that extends beyond the distal end of the balloon catheter 90) to allow the endoscope to visualize the tissue wall. Lumen 110 is separate from the inside of the visualization catheter 100 so that it can be reused. Visualization catheter 100 further includes lumen 112 for receiving pull line 46, which extends outwardly from catheter 100 for control by a control unit as discussed below.

As indicated above, visualization catheter 100 further includes expandable structure 180 that is secured to the end visualization catheter 100. The expandable structure 180 comprises a balloon 182 (as known to those skilled in the art) as shown in FIGS. 1-3. Balloon 182 is attached to the distal end of visualization catheter 100 and fixed within it or alternatively to the surface thereof. With either design, balloon 182 must be fixed to maintain a seal that will prevent any passage of saline or other fluid when balloon 182 is filled. At the distal end, balloon 182 is fixed to catheter end that serves as the distal end of visualization catheter 100. Because a balloon is used for expansion and visualization, visualization catheter 100 is sometimes referred to as a balloon catheter.

Balloon 182 is preferably made of an opaque material to allow a medical practitioner to see through it to visualize ablation element 90 and the tissue region intended to be ablated. The material of balloon 182 is flexible to accommodate some variation in pulmonary vein anatomy. The diameter of the visualization catheter 100 is approximately 2.6 mm but those skilled in the art know that any diameter will work that will achieve desired results. Catheter end 190 has a diameter that is sized to receive guidewire sheath 80 and guidewire 70. Guidewire sheath 80 passes completely through the expandable structure 180 and through catheter end 170, but it terminates therewith. This enables visualization catheter 100 to translate independently with respect to catheter body 30. However, guidewire 70 is permitted to run completely through catheter body 30 and out front ring 56.

While the expandable structure 180 comprises a balloon 182 in the embodiment shown and described, those skilled in the art know that in alternative embodiments other expandable structures maybe be used to achieve desired results. For example, any clear deformable material such as silicon may be employed to expand and allow visualization. The silicon formed material will incorporate a CMOS sensor and desired fiber optic cables coupled to the sensor for visualization. The silicon may be deployed and maneuvered by axial pressure or by a sheath to contort and position the shape of the silicon as known to those skilled in the art.

Catheter end 190 fits within the recessed portion of front ring 56 (corresponding diameter as catheter end 190) as indicated above. This recessed portion only extends through a portion of front ring 56. Guidewire 70 is free to move independently with respect to the rest of catheter body 30 to control ablation element 90 by way of wires 52a, 52b. Balloon 182 is filled with saline through lumen 108 of visualization 100.

Ablation catheter system 20 via guidewire 70 and sheath 40 is steerable to enable catheter body 30 to be advanced into all four pulmonary veins. When sheath 40 is retracted, catheter body 30 is advanced over wires 52a, 52b will expand to their heat-treated position.

FIG. 6 depicts a side view of ablation therapy system 10 including the ablation catheter system 20 of FIG. 1 and the external operational components for operating the ablation catheter system 20. Specifically, ablation therapy system 10 further includes a control unit 200, inflation unit 230, light generator and visualization unit 240, tube irrigation unit 250, RF transceiver 260, display 270 coupled to RF transceiver 260, intracardiac electrogram 280 and display 290 coupled to intracardiac electrogram 280.

These components are shown as lines that are connected to catheter body 30. The lines represent tubes and cables known to those skilled in the art as discussed in more detail below. In one embodiment, many of the tubes and cables that extend from catheter body 30 may enter a coupling mechanism or handle (not shown) as known to those skilled in the art. The handle acts as a junction for such tubes and cables to enable a medical practitioner to quickly and easily connect the ablation catheter system 20 components. Alternatively, some or all of the tubes and cables may be coupled, without such a handle, separately to such operational components described above.

Control unit 200 is coupled to guidewire 70. The medical practitioner uses the control unit 200 to control the movement of guidewire 70. Guidewire 70 can be rotated, advanced and/or retracted to thereby selectively control support arms 52. Control unit 200 may also be used to control visualization catheter 100 or it may be manipulated manually as known to those skilled in the art.

FIG. 7A depicts control 200 unit in FIG. 6 in accordance with an embodiment of the present invention. In FIG. 7A, control unit 200 includes handle 202 and it comprises a lever 204 positioned midway between the ends of handle 202 and wheel 206 located on an end of the handle 202. Handle 202 has a lumen to receive guidewire 70. Guidewire 70 is shown in dotted lines in FIG. 7A. In order to set up control unit 200 with guidewire 70 for operation, the medical practitioner slides handle 202 over guidewire 70 and rotates (i.e., tightens) lever 204 to clamp against guidewire 70 as known to those skilled in the art. In an alternative construction, wheel 206 may be a separate component and threaded or snap fitted onto the handle 202. Handle 202 also includes a lumen to receive flexible line 124 of pivot mechanism 120. Flexible line 124 is also shown in dotted line in FIG. 7A. Flexible line 124 is tied to a small grasping ball/knob as shown. Handle 202 may include a gear or pulley mechanism to assist in the operation of flexible line 124 as known those skilled in the art (e.g., secure and release line 124). Handle 202 also includes a lumen for receiving pull line 46. Pull line 46 is also shown extending through tied to ball or knob. Handle 202 may also include a gear or pulley mechanism to assist with the operation of the pull line 46 as known to those skilled in the art to move ablation element 90 along arm 52a. Handle 202 may also be adapted to control visualization catheter 100 or it may be controlled manually as known to those skilled in the art.

In operation, when wheel 206 rotates, handle 202 and hence guidewire 70 rotates. While holding catheter body 30, the medical practitioner may push or pull wheel 206 to expand or contract wires 52a, 52b (support arms 52). The medical practitioner may control flexible line 124 and/or pull line 46 through control unit 200 to cause support arms 52 to pivot and/or to make ablation element 90 slide along wire 52a, respectfully. Support arms 52 will return to an un-pivoted position when the practitioner releases flexible line 124. Ablation element 90 will return to a resting position adjacent to front ring 56 when the practitioner releases pull line 46. Control unit 200 shown in FIG. 7A is one embodiment for controlling guidewire 70.

Figure 7B:
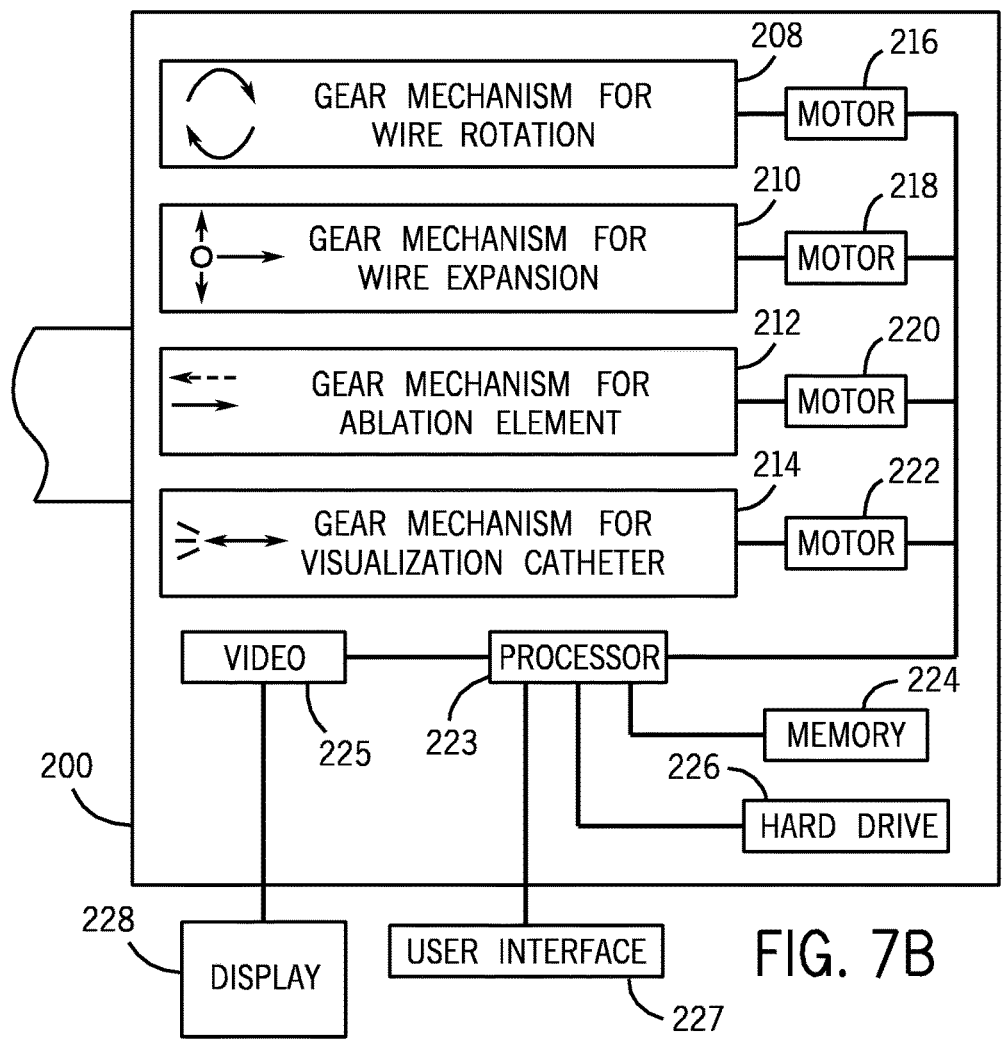
FIG. 7B depicts the control unit in FIG. 6 in accordance with another embodiment of the present invention.

FIG. 7B depicts control unit 200 in FIG. 6 in accordance with another embodiment of the present invention. In detail, FIG. 7B depicts a control unit that is computerized and motorized to control the operation of the components of ablation catheter system 20. In FIG. 7B, control unit 200 includes a plurality of gear mechanism 208-212 for operating, i.e., driving the components of ablation catheter system 20, thereby moving ablation element 90 and visualization catheter 100 as known to those skilled in the art. Specifically, gear mechanism 208 is for wire 52a rotation and gear mechanism 210 is for wires 52a, 52b expansion (by way of central guidewire 70). Gear mechanism 212 is for controlling the movement of ablation element 90 along wire 52a (via pull line 46). Gear mechanism 214 is for moving visualization catheter 100. These gear mechanisms may be implemented using a ratchet system (similar to a wrench) and/or screw or other mechanism as known to those skilled in the art. For example, coordinated rotation and translation together, may be achieved by a screw turn or click to enable ablation element 90 to essentially move diagonally (to effect diagonal lesion formation). Gear mechanism 212 may also include an inflation unit (instead of inflation unit 230 as described above).

Control unit 200 includes motors 216, 218, 220, 222 for controlling the operation of gear mechanisms 208, 210, 212, 214, respectively. Control unit 200 further includes processor 223 for executing computer programs to control the operation of motors 216-222 (and hence ablation element 90) and memory 224 connected to processor 223 for storing computer program to be executed by processor 223 as known to those skilled in the art. Control unit 200 further includes hard drive 225 as a storage device for storing measured values etc. and video card 226 for connecting to display 228. Control unit 200 will also include user interface 227 that may be manipulated by the medical practitioner to control the operation of control unit 200. User interface 227 may be a joystick or other mechanism to effect instructions to the processor. While the components of control unit 200 are described herein, those skilled in the art know that other components may be included or excluded to achieve desired results.

While two exemplary embodiments of control unit 200 have been described herein, those skilled in the art know that other control units or other mechanisms may be used to achieve desired results.

Returning to FIG. 6, inflation unit 230 is connected to lumen 108 to provide fluid to visualization catheter 100. Inflation unit 230 delivers fluid to lumen 108 through interface tubing (not shown) as known to those skilled in the art. Saline is preferably used to inflate the balloon 182. Saline enables the medical practitioner to see through the balloon 182. However, those skilled in the art know that fluids other than saline may be used to achieve desired results.

Light generator and visualization unit 240 is coupled to light source 150 and visualization source 160 via an optical coupler interface 242 (shown in dotted line) to provide light to such light source 150 and camera and/or other technologies as known to those skilled in the art for visualizing a region using visualization source 160. In addition, Light generator and visualization unit 240 will incorporate technology to take images and/or video as known by those skilled in the art.

Ablation therapy system 10 may also include other components and/or technologies necessary for using an endoscope as known to those skilled in the art (and ablation catheter system 20 is designed with a lumen to receive an endoscope).

Tube irrigation unit 250 is coupled to RF irrigation tubing 140 for providing saline or other fluids to cool ablation element 90 during ablation. Tube irrigation unit 250 may be a handheld pump, motorized pump or other mechanism that pumps fluid through irrigation tubing 120 as known to those skilled in the art.

RF transceiver 260 as known to those skilled in the art is coupled to RF and thermocouple wires 130 for delivering an RF energy signal to ablation element 90 and to measuring temperature off of ablation element 90. RF transceiver 260 may include an internal display for displaying RF settings, energy readings, sensor readings and other information or such information may be displayed on external display 270. Display 270 is used to display signals representing electrical activity of the target tissue.

Intracardiac electrogram 280 as known to those skilled in the art is coupled to RF and thermocouple wires 130 for measuring electrical activity of target tissue as known by those skilled in the art. Display 290 is coupled to intracardiac electrogram 260 and it is used in to display measured readings.

While the components identified above are described for ablation therapy system 10, those skilled in the art know that additional components or less components may be employed in accordance with other embodiments of the present invention. For example, display 290 may not be needed, if intracardiac electrogram 280 has a display. In alternative embodiments, ablation catheter system 20 may incorporate different components for achieving desired results. For example, ablation catheter system 20 may incorporate one or more wheels (or other rotation elements) coupled to RF ablation element 90 with motorized capability (components) as known to those skilled in the art to enable RF ablation element 90 to move along heart tissue. That is, the wheels will rotate and travel along the tissue, thereby pulling RF ablation element 90 along the tissue. The motorized components (e.g., spin motor) will be under the control of control unit 200.

Motion/operation. The following describes the motion/operation of ablation catheter system 20 shown in the figures.

Rotation of RF ablation element 90 independent of balloon 182. Central guidewire 70 is rotated at the proximal end of the catheter body 30 by control unit 200 180 degrees in each direction from its initial point for a full 360 degrees. If a medical practitioner rotates central guidewire 70, front ring 56 rotates which results subsequently rotates front ring 54, support arms 52 (wires 52a, 52b) and ablation element 90.

Expanding support arms 52. The medical practitioner advances catheter body 30 through catheter sheath 40, until support arms 52 move past the distal end of catheter body 30. This will cause support arms 52 to assume their curved position (e.g., heat treated position). If further expansion is necessary, catheter body 30 is held in a fixed position and central guidewire 70 is retracted using control unit 200. This force pulls front ring 56 towards balloon 182, and as catheter body 30 and rear ring 54 are fixed, it will increase the curvature of support arms 52 shifting RF ablation element 90 to a higher position.

Expanding balloon 182. Inflation unit 230 delivers saline through lumen 108 of visualization catheter 100 to fill balloon 182 with saline resulting in its expansion.

Rotation of RF ablation element 90 in conjunction with balloon 182. Central guidewire 70 is fixed to catheter body 30 externally via control unit 200 and rotated together proximally, resulting in rotation of both RF ablation element 90 (as previously described) and balloon 182 distally.

Advancing and/or rotating balloon 182 independent of catheter body 30, ablation element 90 and front ring 56. While catheter body 30 and central guidewire 70 are fixed, the medical practitioner may advance or rotate visualization catheter 100 thus allowing balloon 182 to move independently of catheter body 30, RF ablation element 90 and front ring 56.

FIG. 8 depicts an enlarged cross-sectional view of the ablation element along line 8-8 in FIG. 2. This is described above.

FIG. 9 depicts an enlarged side view of the distal section of the ablation catheter system 20 of FIG. 1 in accordance with an alternative embodiment of the present invention. In this embodiment, catheter ablation system 20 includes guidewire 70 as describe above. However, guidewire 70 is a separate component that is not initially fixed to catheter body 30. Guidewire 70 is first advanced into the heart as known by those skilled in the art. Then, catheter body 30 incorporating visualization catheter 100 is advanced over guidewire 70. In this respect, the guidewire 70 acts a true guide. However, guidewire 70 includes spring 75 that expands into a complementary sized recess within the lumen of front ring 56 when catheter body 30 is advanced into place. The ablation catheter system 20 then functions similarly as described above.

FIG. 10 depicts a cross-sectional view of an ablation catheter system along line 5-5 in FIG. 2 in accordance with another embodiment of the present invention. In this embodiment, lumen 108 of visualization catheter 100 encompasses, i.e., surrounds several lumens and components that appeared in other parts of visualization catheter 100 in the embodiment described above. In particular, lumen 108 encompasses light source 150 and visualization source 160 respectfully as describe above and guidewire sheath 80 and guidewire 70. The remaining structure is similar to that shown in FIG. 4.

Figure 11A:
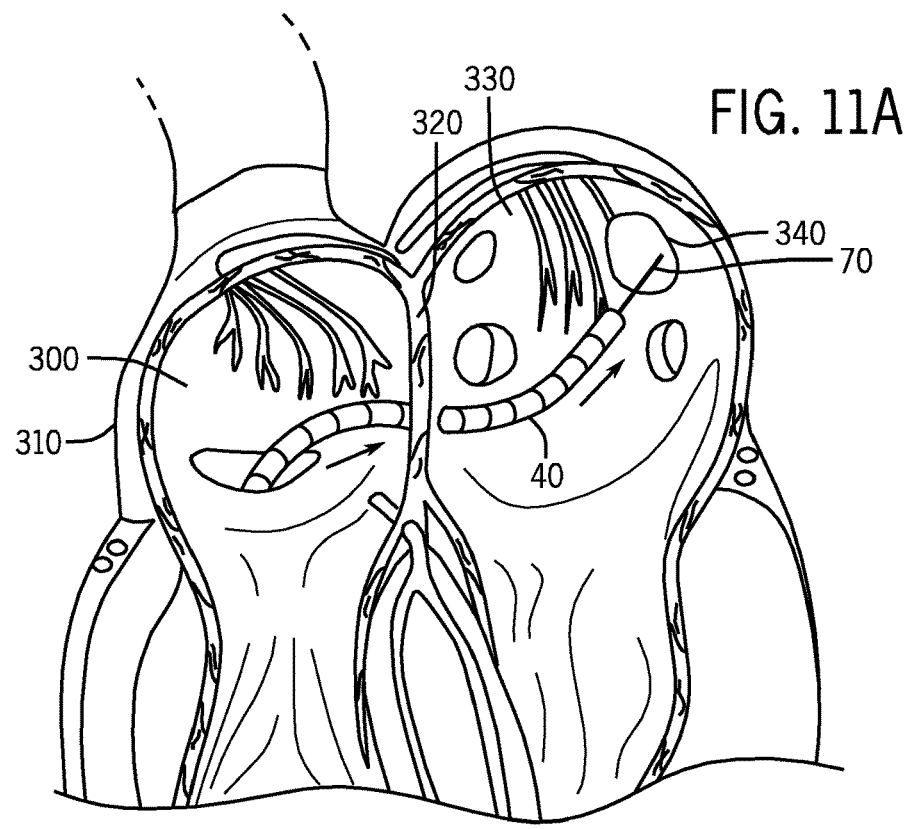
Figure 11B:
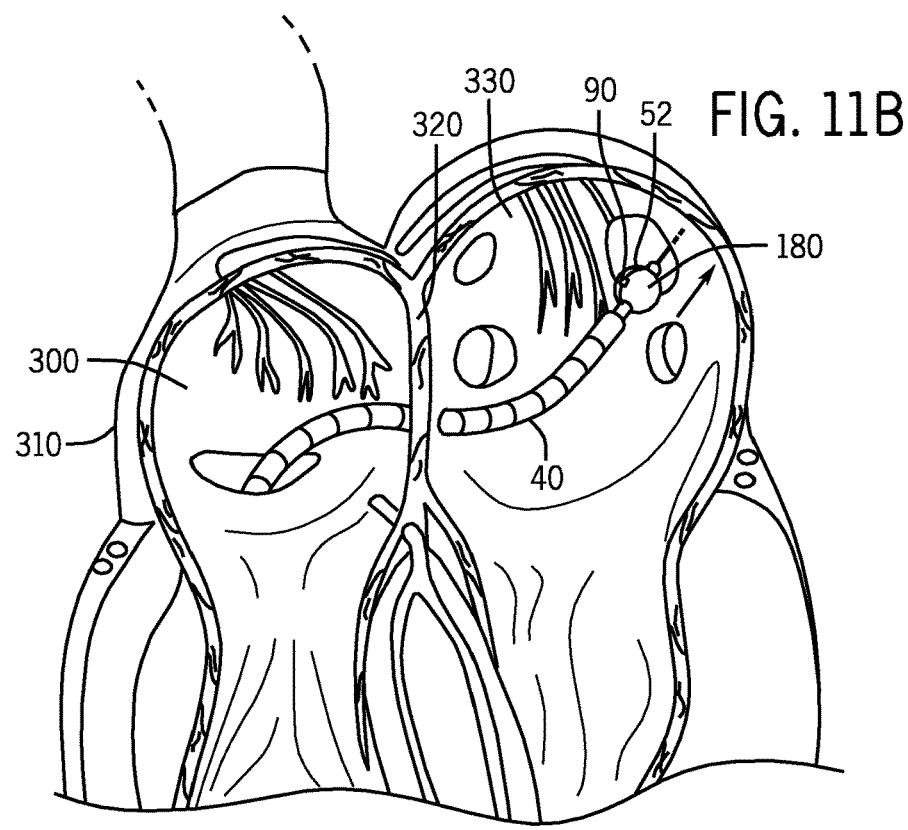

Reference is now made to FIGS. 11A-11E. FIGS. 11A-11E depict selected application steps of a method of using the ablation therapy system 10 in FIG. 6. In the beginning stages of the ablation procedure, ablation catheter system 20 is inserted in a blood vessel (not shown) that leads to left atrium 330 of heart 310 as known to those skilled in the art. The distal end of guidewire 70 (permanent part of ablation catheter system 20 in this embodiment) and composition of catheter sheath 40 act as a guide to enable ablation catheter 20 to advance through the blood vessel and heart. Ablation catheter system 20 is passed through an opening created in the septum 320 that separates the right and left atria into left atrium 330. In FIG. 11A, ablation catheter system 20 is advanced to a position within atrium 330 adjacent a pulmonary vein 340. Ablation catheter system 20 is shown in an un-deployed configuration wherein sheath 40 covers wires 52a, 52b (support arms 52) and they have not been retracted to expose wires 52a, 52b (support arms 52). In FIG. 11B, sheath 40 is shown in a retracted position wherein wires 52a, 52b (support arms 52) of ablation catheter system 20 are expanded to their biased shape (e.g. pre-heat treated shape as shown).

FIG. 11C depicts ablation catheter system 20 in an advanced position wherein wires 52a, 52b (support arms 52) encircle the opening or entry of the pulmonary vein 340 known as the ostium, and a first tissue site is ablated by RF energy (heating) of the contacted tissue. As depicted in FIG. 11C, ablation element 90 is positioned against the target tissue along with the assistance of balloon 182 (of expandable structure 180). That is, balloon 182 is positioned and expanded against wires 52a, 52b (support arms 52) to ensure that ablation element 90 is firmly against the tissue. This is shown detail in FIG. 12. FIG. 12 depicts an enlarged perspective view of ablation catheter system 20 in FIG. 11C. In FIG. 11, balloon catheter 100 is maneuvered to position the balloon 182 against wires 52a, 52b. In this respect, balloon 182 is used to maintain ablation element 90 in place against the target tissue as well to sufficiently block blood to enable a medical practitioner to visualize the tissue surface.

FIG. 11D depicts ablation catheter system 20 in an advanced position wherein wires 52a, 52b encircle the opening or entry of the pulmonary vein 340 known as the ostium, and second tissue site is ablated by RF energy delivered to ablation element 90. As depicted in FIG. 11D, ablation element 90 is positioned against a second target tissue site along with the assistance of balloon 182. Wires 52a, 52b (of support arms 52) are shown pivoted and expanded to ensure that ablation element 90 is positioned against the second tissue site. Ablation catheter system 20 is maneuvered and tissue is ablated at other tissue sites. The intended result is a substantially uniform continuous ablation line with adjacent lesions circumferentially around the pulmonary vein as visualized by an endoscope camera for example.

Figure 11E:
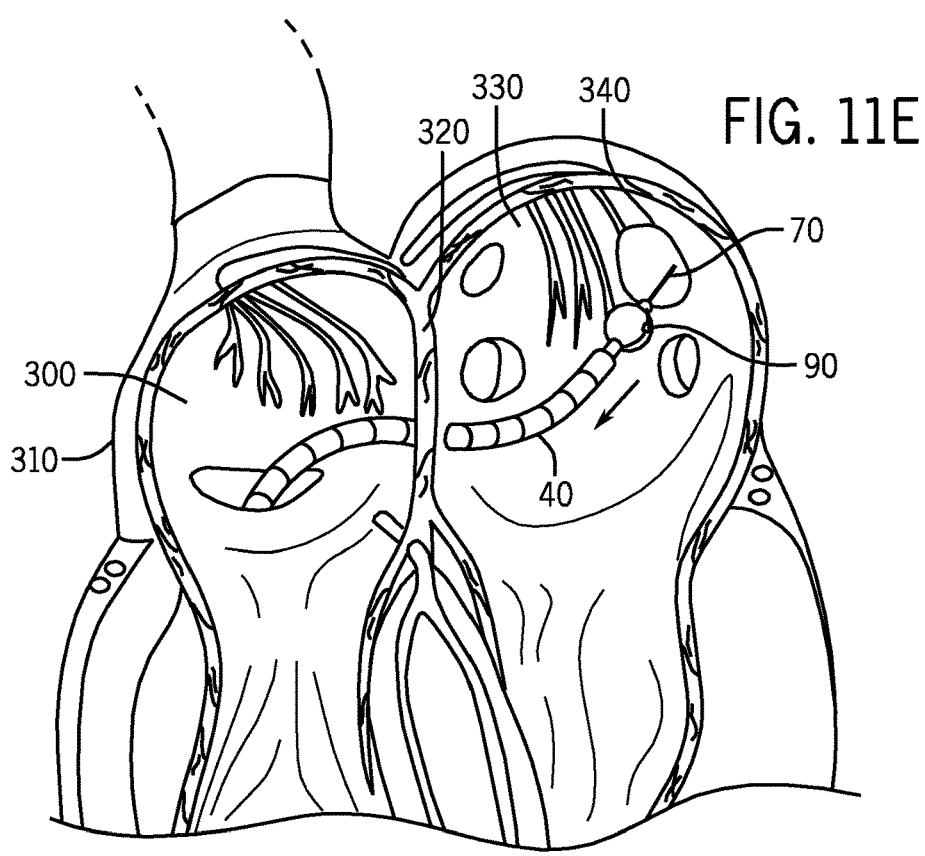
Figure 12:
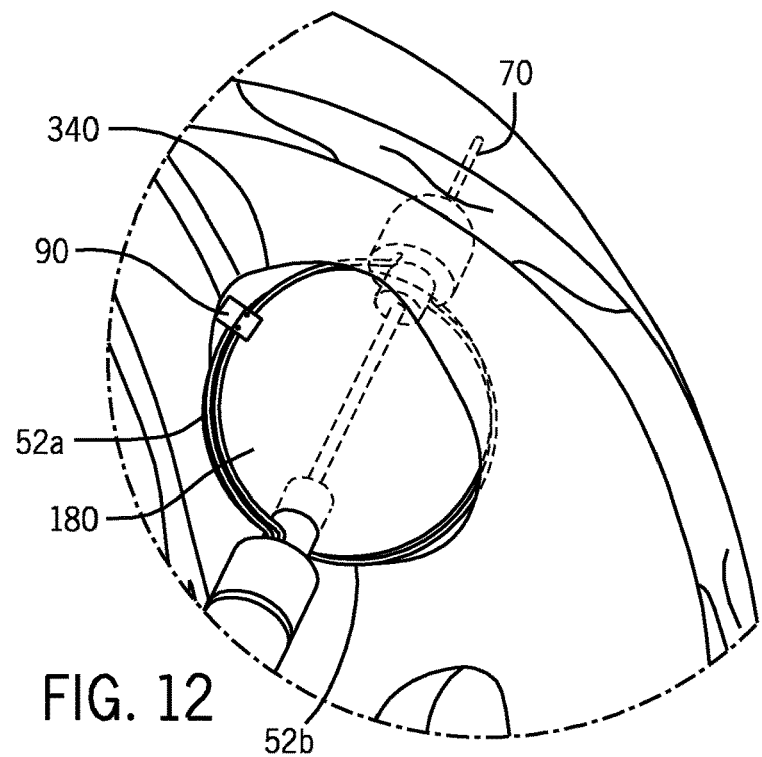
FIG. 12 depicts an enlarged perspective view of ablation catheter system 20 in FIG. 11C.

FIG. 11E depicts ablation catheter system 20 in a retracted position wherein wires 52a, 52b are expanded in their natural (e.g., heated treated) position (as if they were first exposed when sheath 40 is removed).

In the embodiments shown and described herein, balloon 82 aids in the position of support arms 52 and RF ablation element 90. However, in alternative embodiments, support arms 52 may be used to deploy, shape, reposition and re-deform balloon 182 as known to those skilled in the art.

Figure 13:
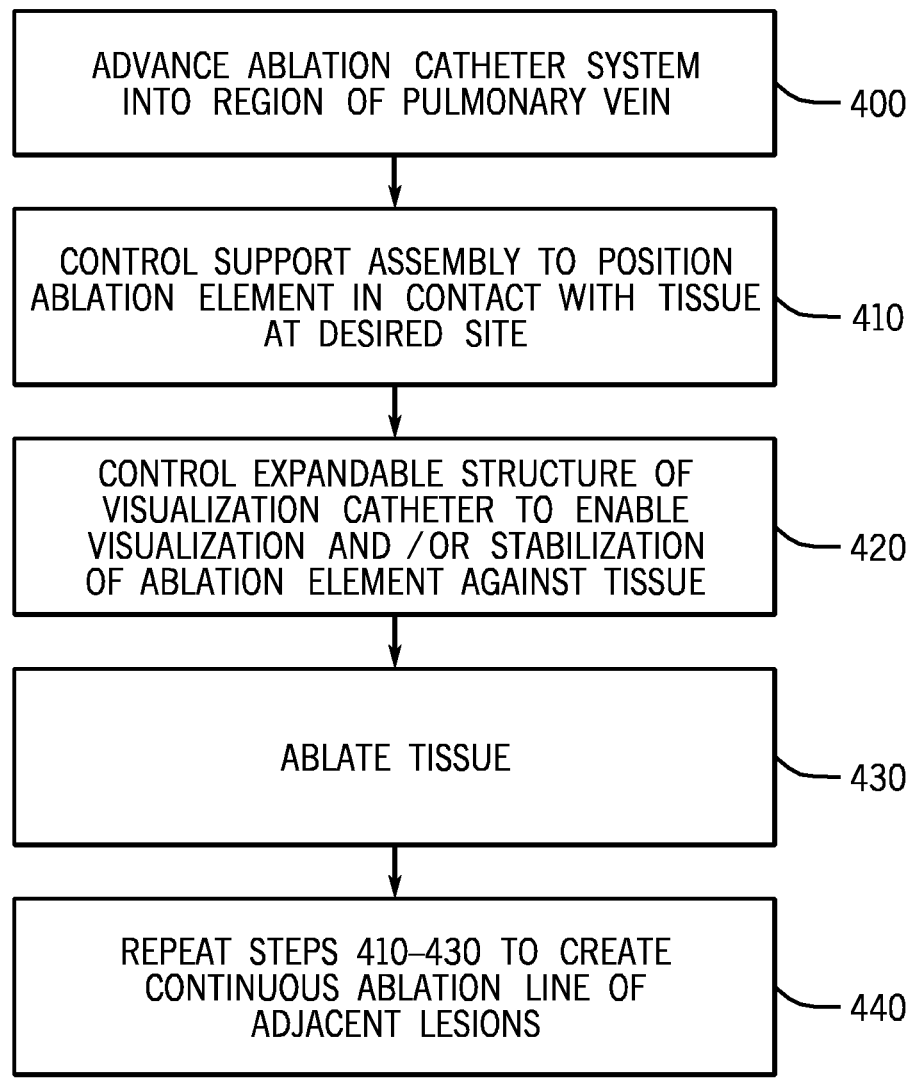
FIG. 13 depicts high-level steps of the method for treating AF using the ablation therapy system in FIG. 6 including the ablation catheter system and operational components.

FIG. 13 depicts high-level steps of the method for treating AF using the ablation therapy system 10 in FIG. 6 including the ablation catheter system 20 and operational components. In such form, the method begins at step 400 wherein ablation catheter system 20 is advanced into the region of the pulmonary vein 340. At step 410, the support assembly 50 is controlled by control unit 200 to maneuver and position ablation element 90 in contact with the tissue at a desired site. Expandable structure 180 (balloon 182) is controlled to enable visualization of the target tissue and/or stabilize the ablation element 90 against target tissue at step 420. Light source 150 and visualization source 160 are employed. The method proceeds to step 430 wherein the tissue is ablated. The method moves to step 430 wherein steps 410-430 are repeated. In this respect, the method produces a continuous ablation line of lesions without gaps. These are the high-level steps of the method for treating AF, but those skilled in the art know that some or other steps (possibly in different order) may be employed in accordance with the present invention. For example, the electrical activity or trigger of the target tissue may be measured, if needed, using ablation element 90, RF and thermocouple wires 130 and intracardiac electrogram 260 as described above.

Figure 14:
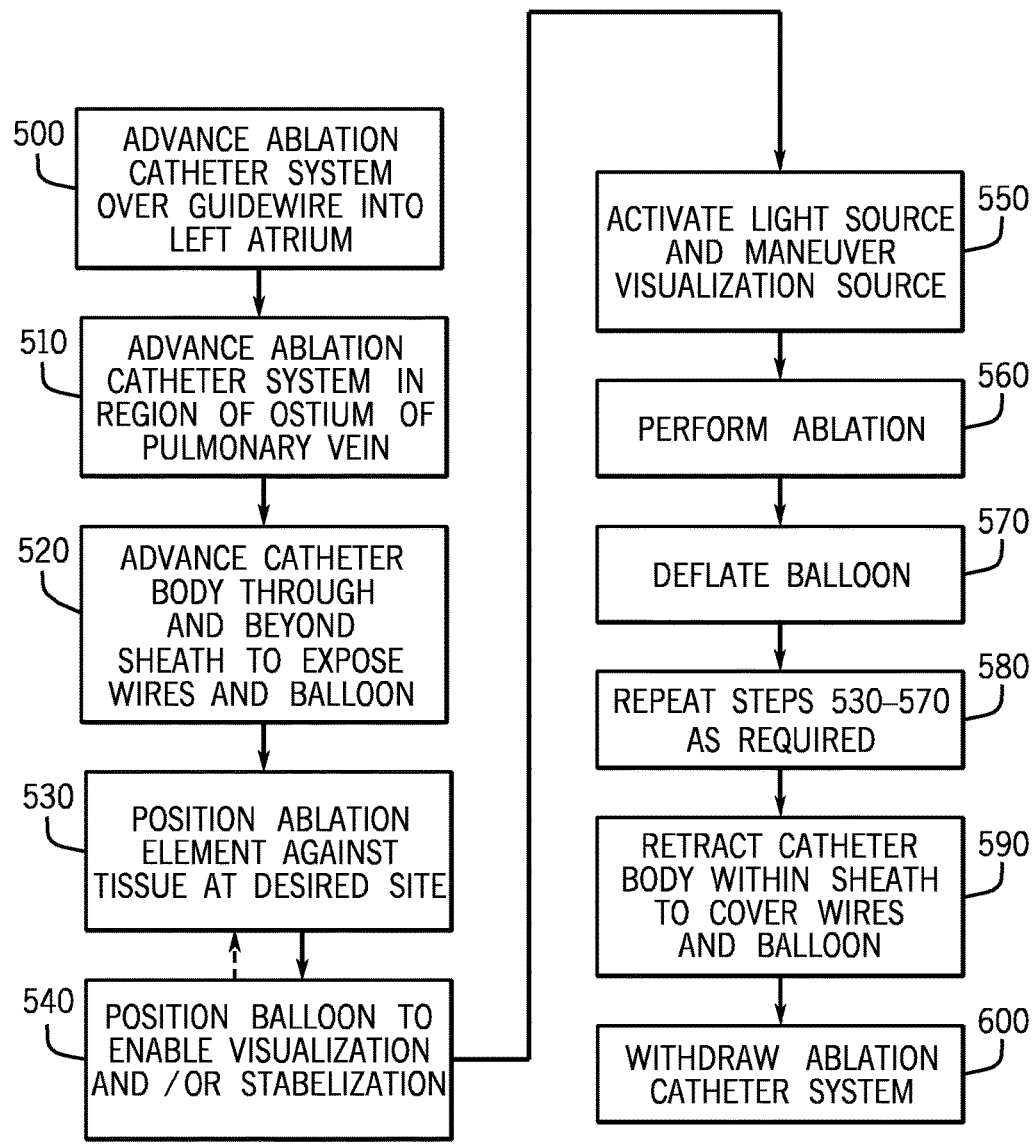
FIG. 14 depicts the steps of the method for treating AF using the ablation therapy system in FIG. 6 including the ablation catheter system and operational components.

FIG. 14 depicts the steps of the method for treating AF using the ablation therapy system in FIG. 6 including the ablation catheter system and operational components. In particular, the method beings (again) with step 500 and 510 wherein ablation catheter system 20 is advanced into the left atrium of the heart and into the region of the ostium of the pulmonary vein. At step 520, the catheter body 30 is advanced beyond catheter sheath 40 to expose wires 52*a*, 52*b* and balloon 182. The sheath is held while the catheter body 30 is advanced. Alternatively, sheath 40 may be pulled while catheter body 30 is held in place. Next, ablation element 90 is maneuvered and positioned against the tissue at the desired site at step 530. This is accomplished when a medical practitioner uses control unit 200 to manipulate wires 52*a*, 52*b*. At step 540, the balloon 182 is positioned (including expansion) to enable visualization. Balloon 182 may also be used to stabilize ablation element 90 against atrial tissue. While steps 530 and 540 are shown and described in that order, those skilled in the art know that in practice, these steps may be repeatedly performed in that order or in reverse to ensure proper positioning of both the ablation element 90 and balloon 82. Hence, FIG. 14 is shown with a dotted arrow line from step 540 to 530. However, the medical practitioner must take care to ensure that the pull line 46 extending from visualization catheter 100 does not incidentally pull ablation element 90 out of place when catheter 100 is moved.

Next, light source 150 and visualization source 160 are activated for illuminating and visualizing a region at step 550. The medical practitioner will activate RF transceiver and ablate the tissue with ablation element 90 at step 560. The method moves to step 570, wherein balloon 182 is deflated. At step 580, steps 530-570 are repeated in attempt to create a substantially uniform continuous ablation line with adjacent lesions (without gaps) circumferentially around the pulmonary vein. The medical practitioner may optionally measure electrical activity of targeted tissue sites before or after ablation is performed as described above.

Once completed, Catheter body 30 is retracted within catheter sheath 40 to cover wires 52*a*, 52*b* and balloon 182 and ablation catheter system 20 is withdrawn at steps 590 and 600, respectfully. FIG. 13 illustrates the detailed steps of the method for treating AF using ablation therapy system 10, but those skilled in the art know that less, more or different steps maybe be performed (or possibly in different order) in accordance with the present invention.

Figure 15:
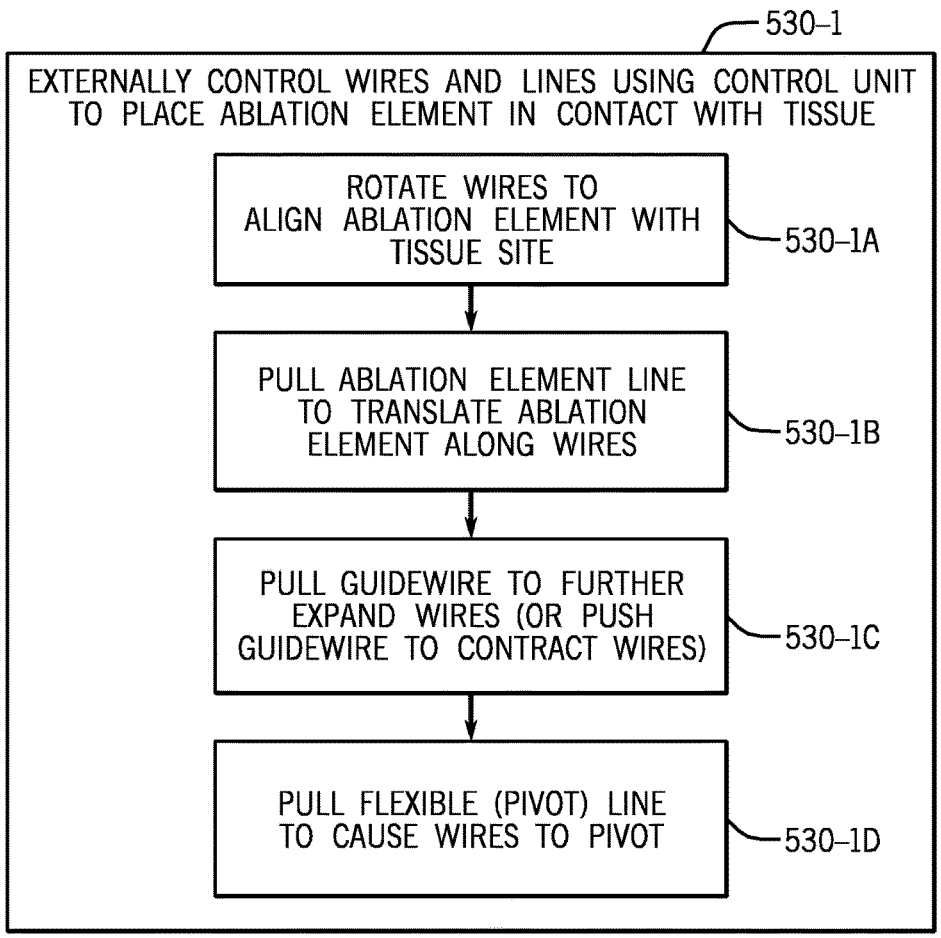
FIGS. 15 and 16 depict an implementation for selected steps of the method depicted in FIG. 14.
Figure 16:
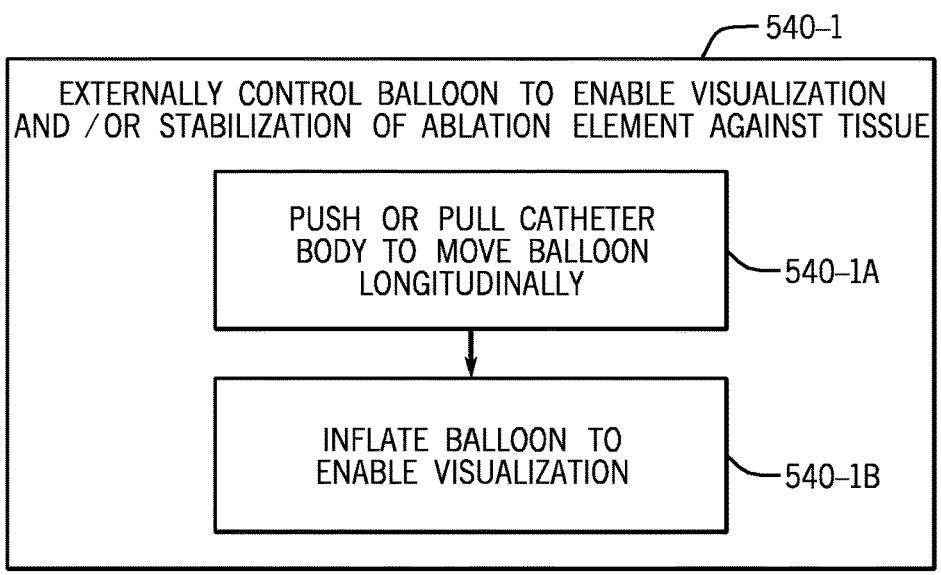

FIGS. 15 and 16 depict an implementation for selected steps of the method depicted in FIG. 14. In particular, step 530 in FIG. 14 is implemented by step 530-1 in FIG. 15. Specifically, the medical practitioner controls wires 52*a*, 52*b* by using control unit 200 to place ablation element 90 in contact with the tissue. This is done by rotating guidewire 70 to selectively rotate wires 52*a*, 52*b*, to thereby align ablation element 90 with a tissue site at sub-step 530-1A. Pull line 46 is likely adjusted to permit rotation of wires 52*a*, 52*b*. At sub-step 530-1B, pull line 46 is then used to translate ablation element 90 along wire 52*a*. At sub-step 530-1C, guidewire 70 is pulled to further expand wires 52*a*, 52*b* or guidewire 70 is pushed forward to contract wires 52*a*, 52*b* as needed to accurately contact the tissue. Optionally, flexible (pivot) line 124 is pulled to selectively pivot wires 52*a*, 52*b* to ensure an accurate contact between ablation element 90 and the tissue at sub-step 530-1D. Because of the wide range of control, ablation element 90 is able to move diagonally to coordinate proper lesion line formation.

Referring to FIG. 16, step 540 in FIG. 13 is implemented by step 540-1 in FIG. 15. The medical practitioner controls balloon 182 to enable the physician to visualize the tissue site and/or stabilize the ablation element against the tissue. This is done by sub-steps 540-1A and 540-1B. In step 540-1A, the medical practitioner advances or retracts visualization catheter 100 to move balloon 182 longitudinally forward and back. At sub-step 540A-2, balloon 182 is inflated to enable visualization (e.g., block blood) and/or to stabilize wires 52*a*, 52*b* against the tissue. (As indicated above, the sub-steps shown in FIG. 15 may be alternated with sub-steps in FIG. 16 in practice during the procedure.) FIGS. 15 and 16 illustrate the detail implementation of selected steps of the method for treating AF but those skilled in the art know that less, more or different steps maybe be performed (or possibly in different order) in accordance with the present invention.

It is to be understood that the disclosure teaches examples of the illustrative embodiments and that many variations of the invention can easily be devised by those skilled in the art after reading this disclosure and that the scope of the present invention is to be determined by the claims below.

What is claimed is:

1. An ablation therapy system including an ablation catheter system for treating atrial fibrillation (AF), the ablation catheter system comprising:
   (a) a catheter body including a lumen receiving a visualization catheter;
   (b) an ablation element configured to ablate tissue at a region in a patient's heart having abnormal electrical activity;
   (c) a support assembly supported by the catheter body, the support assembly including a lumen receiving the visualization catheter,
      wherein the ablation element is supported on the support assembly for movement therealong so as to enable a user of the ablation therapy system to control the movement and the support assembly is supported for rotational or pivoting movement so as to enable the user to selectively control the rotation or pivoting movement independently with respect to the catheter body and so as to enable the user to selectively position the ablation element along the support assembly and to select the region in the heart that is to be ablated,
      wherein the support assembly comprises a support arm for supporting the ablation element, and
      wherein the support assembly includes front and rear rings, each ring having a hole for receiving an end of the support arm, the rear ring configured to rotate with respect to the catheter body, the rear ring including the lumen of the support assembly receiving the visualization catheter,
      wherein the visualization catheter having an end that is configured to fit within a recessed portion of the front ring of the support assembly; and
   (d) a pivot mechanism configured to cause the support arm to pivot with respect to the catheter body, wherein the pivot mechanism comprises a flexible line extending from the end of the visualization catheter therethrough, whereby tension on the flexible line causes support arm to pivot with respect to the catheter body.

2. The ablation therapy system of claim 1 wherein the support arm is configured to expand outwardly.

3. The ablation therapy system of claim 1 wherein the support arm comprises a wire.

4. The ablation therapy system of claim 1 wherein the ablation element is configured to slide along the support arm.

5. The ablation therapy system of 1 further comprising a guidewire passing through the lumen of the catheter body and the lumen of the rear ring, the guidewire having an end fixed to the front ring, whereby guidewire rotation with respect to the catheter body simultaneously rotates the front ring, rear ring and support arm.

6. The ablation therapy system of 1 further comprising a guidewire passing through the lumen of the catheter body and the lumen of the rear ring, the guidewire having an end fixed to the front ring, whereby guidewire retraction or advancement simultaneously expands or compresses the support arm, respectively.

7. The ablation therapy system of claim 1 further comprising the visualization catheter configured to pass through the lumen of the catheter body and the lumen of the support assembly, respectively.

8. The ablation therapy system of claim 7 wherein the visualization catheter includes an expandable structure configured to expand and stabilize the ablation element against the tissue of the heart.

9. The ablation therapy system of claim 1 further including a control unit for controlling the operation of the ablation catheter system.

10. An ablation therapy system comprising:
(a) an ablation catheter system configured for treating atrial fibrillation (AF), the ablation catheter system comprising:
1) a catheter body having a lumen receiving a visualization catheter;
2) an ablation element configured to ablate tissue in a region in a patient's heart having abnormal electrical activity;
3) a support assembly supported by the catheter body, the support assembly including a second lumen receiving the visualization catheter, wherein the ablation element supported on the support assembly for movement therealong so as to enable a user of the ablation therapy system to control the movement and the support assembly is supported for rotational or pivoting movement independently with respect to the catheter body so as to enable the user to selectively position the ablation element along the support assembly and to select the region in the heart that is to be ablated,
wherein the support assembly comprises a support arm for supporting the ablation element,
wherein the support assembly comprises a support arm and front and rear rings, each ring having a hole for receiving an end of the support arm, the rear ring configured to rotate with respect to the catheter body, the rear ring including the lumen of the support assembly for receiving the visualization catheter, wherein the visualization catheter has an end that is configured to fit within the front ring of the support assembly; and
4) a pivot mechanism configured to enable the support arm to pivot with respect to the catheter body, the pivot mechanism comprising a flexible line extending from the end of the visualization catheter therethrough, whereby tension on the flexible line causes support arm to pivot with respect to the catheter body; and
(b) a control unit operatively associated with the support assembly and controlling rotational or pivoting movement thereof so as to enable the user to selectively control rotational and/or pivoting movement of the support assembly independently with respect to the catheter body so as to enable the user to select the region in the heart that is to be ablated.

11. The ablation therapy system 10 wherein the ablation element is configured to slide along the support arm.

12. The ablation therapy system 10 wherein the control unit is configured to enable a user to coordinate sliding of the ablation element along the support arm.

13. The ablation therapy system of claim 10 wherein the support arm is configured to expand outwardly under the control of the control unit.

14. The ablation therapy system of claim 10 wherein the ablation catheter system further comprising the visualization catheter, a pull wire and tension wire, the pull wire and tension wire attached to opposing sides of the ablation element so as to cause the ablation element to move along the support arm, wherein the pull wire extends within visualization catheter.

15. An ablation catheter system for treating atrial fibrillation (AF), the ablation catheter system comprising:
(a) a catheter body including a lumen receiving a visualization catheter;
(b) an ablation element configured to ablate tissue in a region in a patient's heart having an abnormal electrical activity; and
(c) a support assembly supported by the catheter body, the support assembly including a lumen receiving the visualization catheter,
wherein the ablation element supported on the support assembly for movement therealong so as to enable a user of the ablation therapy system to control the movement and the support assembly is supported for rotational or pivoting movement so as to enable the user to selectively control the rotational or pivoting movement independently with respect to the catheter body and so as to enable the user to selectively position the ablation element along the support assembly and select the region in the heart that is to be ablated,
wherein the support assembly comprises a support arm for supporting the ablation element; and
(d) a pull wire and tension wire attached to opposing sides of the ablation element so as to cause the ablation element to move along the support arm, wherein the pull wire extends within the visualization catheter.

16. The ablation catheter system of claim 15 wherein the visualization catheter is configured to move independently with respect to the catheter body and support assembly.

17. The ablation catheter system of claim 15 wherein the visualization catheter includes an expandable structure.

18. The ablation catheter system of claim 15 wherein the support assembly is configured to rotate with respect to the catheter body.

19. An ablation catheter system for treating atrial fibrillation (AF), the ablation catheter system comprising:
a catheter body including a lumen receiving a visualization catheter;
an ablation element configured to ablate tissue at a region in a patient's heart having an abnormal electrical activity;
a support assembly supported by catheter body and the ablation element supported on the support assembly for movement therealong so as to enable a user of the ablation therapy system to control the movement, the support assembly supported for rotational or pivoting movement independently with respect to the catheter body so as to enable the user to selectively position the ablation element along the support assembly and to select the region in the heart that is to be ablated, the support assembly including (1) first and second rings and (2) a support arm having first and second ends mounted to the first and second rings, respectively, wherein the second ring includes a lumen receiving the visualization catheter; and a guidewire passing through the lumen of the catheter body and the lumen of the second ring, the guidewire having an end fixed to the first ring, whereby guidewire rotation with respect to the catheter body simultaneously rotates the first ring, the second ring and the support arm, the visualization catheter having a lumen for receiving the guidewire, thereby enabling the visualization catheter to slide along the guidewire and into the lumen of catheter body.

20. The ablation therapy system of claim 19 further comprising a pull wire and tension wire attached to opposing sides of the ablation element so as to cause the ablation element to move along the support arm.

21. The ablation therapy system of claim 20 comprising the visualization catheter and wherein the pull wire extends within visualization catheter.

* * * * *